United States Patent
Valentine et al.

(10) Patent No.: US 12,004,739 B2
(45) Date of Patent: Jun. 11, 2024

(54) RELOAD ASSEMBLY WITH KNIFE CARRIER LOCKOUT

(71) Applicant: Covidien LP, Mansfield, MA (US)

(72) Inventors: David Valentine, Hamden, CT (US); Joseph Eisinger, Northford, CT (US); Ramiro Cabrera, Cheshire, CT (US); Patrick Mozdzierz, Glastonbury, CT (US); Christopher Penna, Guilford, CT (US); Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 35 days.

(21) Appl. No.: 17/961,742

(22) Filed: Oct. 7, 2022

(65) Prior Publication Data
US 2023/0045604 A1     Feb. 9, 2023

Related U.S. Application Data

(62) Division of application No. 16/890,334, filed on Jun. 2, 2020, now Pat. No. 11,464,510.

(60) Provisional application No. 62/878,789, filed on Jul. 26, 2019.

(51) Int. Cl.
*A61B 17/15* (2006.01)
*A61B 17/068* (2006.01)
*A61B 17/072* (2006.01)
*A61B 17/115* (2006.01)

(52) U.S. Cl.
CPC ...... *A61B 17/0686* (2013.01); *A61B 17/1155* (2013.01); *A61B 2017/07257* (2013.01); *A61B 2017/07285* (2013.01)

(58) Field of Classification Search
CPC ............ A61B 17/1155; A61B 17/0686; A61B 17/072; A61B 2017/07214; A61B 2017/07285
See application file for complete search history.

(56) References Cited

U.S. PATENT DOCUMENTS

| | | |
|---|---|---|
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Nov. 27, 2020, issued in corresponding EP Appln. No. 20 18 7067, 15 pages.

(Continued)

*Primary Examiner* — Gloria R Weeks
(74) *Attorney, Agent, or Firm* — Carter, DeLuca & Farrell LLP

(57) ABSTRACT

A surgical stapling device includes a reload assembly that includes a locking member to retain a knife carrier of the reload assembly in a retracted position after the stapling device is fired. The locking member may be supported on an inner housing portion of the shell housing or on a staple pusher assembly of the reload assembly.

20 Claims, 25 Drawing Sheets

(56) References Cited

U.S. PATENT DOCUMENTS

| | | |
|---|---|---|
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |

(56) References Cited

U.S. PATENT DOCUMENTS

| | | |
|---|---|---|
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |

(56) References Cited

U.S. PATENT DOCUMENTS

| | | | |
|---|---|---|---|
| 7,938,307 B2 | 5/2011 | Bettuchi | |
| 7,942,302 B2 | 5/2011 | Roby et al. | |
| 7,951,166 B2 | 5/2011 | Orban, III et al. | |
| 7,959,050 B2 | 6/2011 | Smith et al. | |
| 7,967,181 B2* | 6/2011 | Viola | A61B 17/072 227/180.1 |
| 7,975,895 B2 | 7/2011 | Milliman | |
| 8,002,795 B2 | 8/2011 | Beetel | |
| 8,006,701 B2 | 8/2011 | Bilotti et al. | |
| 8,006,889 B2 | 8/2011 | Adams et al. | |
| 8,011,551 B2 | 9/2011 | Marczyk et al. | |
| 8,011,554 B2 | 9/2011 | Milliman | |
| 8,016,177 B2 | 9/2011 | Bettuchi et al. | |
| 8,016,858 B2 | 9/2011 | Whitman | |
| 8,020,741 B2 | 9/2011 | Cole et al. | |
| 8,025,199 B2 | 9/2011 | Whitman et al. | |
| 8,028,885 B2 | 10/2011 | Smith et al. | |
| 8,038,046 B2 | 10/2011 | Smith et al. | |
| 8,043,207 B2 | 10/2011 | Adams | |
| 8,066,167 B2 | 11/2011 | Measamer et al. | |
| 8,066,169 B2 | 11/2011 | Viola | |
| 8,070,035 B2 | 12/2011 | Holsten et al. | |
| 8,070,037 B2 | 12/2011 | Csiky | |
| 8,096,458 B2 | 1/2012 | Hessler | |
| 8,109,426 B2 | 2/2012 | Milliman et al. | |
| 8,109,427 B2 | 2/2012 | Orban, III | |
| 8,113,405 B2 | 2/2012 | Milliman | |
| 8,113,406 B2 | 2/2012 | Holsten et al. | |
| 8,113,407 B2 | 2/2012 | Holsten et al. | |
| 8,123,103 B2 | 2/2012 | Milliman | |
| 8,128,645 B2 | 3/2012 | Sonnenschein et al. | |
| 8,132,703 B2 | 3/2012 | Milliman et al. | |
| 8,136,712 B2 | 3/2012 | Zingman | |
| 8,146,790 B2 | 4/2012 | Milliman | |
| 8,146,791 B2 | 4/2012 | Bettuchi et al. | |
| 8,181,838 B2 | 5/2012 | Milliman et al. | |
| 8,192,460 B2 | 6/2012 | Orban, III et al. | |
| 8,201,720 B2 | 6/2012 | Hessler | |
| 8,203,782 B2 | 6/2012 | Brueck et al. | |
| 8,211,130 B2 | 7/2012 | Viola | |
| 8,225,799 B2 | 7/2012 | Bettuchi | |
| 8,225,981 B2 | 7/2012 | Criscuolo et al. | |
| 8,231,041 B2 | 7/2012 | Marczyk et al. | |
| 8,231,042 B2 | 7/2012 | Hessler et al. | |
| 8,257,391 B2 | 9/2012 | Orban, III et al. | |
| 8,267,301 B2 | 9/2012 | Milliman et al. | |
| 8,272,552 B2 | 9/2012 | Holsten et al. | |
| 8,276,802 B2 | 10/2012 | Kostrzewski | |
| 8,281,975 B2 | 10/2012 | Criscuolo et al. | |
| 8,286,845 B2 | 10/2012 | Perry et al. | |
| 8,308,045 B2 | 11/2012 | Bettuchi et al. | |
| 8,312,885 B2 | 11/2012 | Bettuchi et al. | |
| 8,313,014 B2 | 11/2012 | Bettuchi | |
| 8,317,073 B2 | 11/2012 | Milliman et al. | |
| 8,317,074 B2 | 11/2012 | Ortiz et al. | |
| 8,322,590 B2 | 12/2012 | Patel et al. | |
| 8,328,060 B2 | 12/2012 | Jankowski et al. | |
| 8,328,062 B2 | 12/2012 | Viola | |
| 8,328,063 B2 | 12/2012 | Milliman et al. | |
| 8,343,185 B2 | 1/2013 | Milliman et al. | |
| 8,353,438 B2 | 1/2013 | Baxter, III et al. | |
| 8,353,439 B2 | 1/2013 | Baxter, III et al. | |
| 8,353,930 B2 | 1/2013 | Heinrich et al. | |
| 8,360,295 B2 | 1/2013 | Milliman et al. | |
| 8,365,974 B2 | 2/2013 | Milliman | |
| 8,403,942 B2 | 3/2013 | Milliman et al. | |
| 8,408,441 B2 | 4/2013 | Wenchell et al. | |
| 8,413,870 B2 | 4/2013 | Pastorelli et al. | |
| 8,413,872 B2 | 4/2013 | Patel | |
| 8,418,905 B2 | 4/2013 | Milliman | |
| 8,418,909 B2 | 4/2013 | Kostrzewski | |
| 8,424,535 B2 | 4/2013 | Hessler et al. | |
| 8,424,741 B2 | 4/2013 | McGuckin, Jr. et al. | |
| 8,430,291 B2 | 4/2013 | Heinrich et al. | |
| 8,430,292 B2 | 4/2013 | Patel et al. | |
| 8,453,910 B2 | 6/2013 | Bettuchi et al. | |
| 8,453,911 B2 | 6/2013 | Milliman et al. | |
| 8,485,414 B2 | 7/2013 | Criscuolo et al. | |
| 8,490,853 B2 | 7/2013 | Criscuolo et al. | |
| 8,511,533 B2 | 8/2013 | Viola et al. | |
| 8,551,138 B2 | 10/2013 | Orban, III et al. | |
| 8,567,655 B2* | 10/2013 | Nalagatla | H04B 7/0673 227/19 |
| 8,579,178 B2 | 11/2013 | Holsten et al. | |
| 8,590,763 B2 | 11/2013 | Milliman | |
| 8,590,764 B2 | 11/2013 | Hartwick et al. | |
| 8,608,047 B2 | 12/2013 | Holsten et al. | |
| 8,616,428 B2 | 12/2013 | Milliman et al. | |
| 8,616,429 B2 | 12/2013 | Viola | |
| 8,622,275 B2 | 1/2014 | Baxter, III et al. | |
| 8,631,993 B2 | 1/2014 | Kostrzewski | |
| 8,636,187 B2 | 1/2014 | Hueil et al. | |
| 8,640,940 B2 | 2/2014 | Ohdaira | |
| 8,662,370 B2 | 3/2014 | Takei | |
| 8,663,258 B2 | 3/2014 | Bettuchi et al. | |
| 8,672,931 B2 | 3/2014 | Goldboss et al. | |
| 8,678,264 B2 | 3/2014 | Racenet et al. | |
| 8,684,248 B2 | 4/2014 | Milliman | |
| 8,684,250 B2 | 4/2014 | Bettuchi et al. | |
| 8,684,251 B2 | 4/2014 | Rebuffat et al. | |
| 8,684,252 B2 | 4/2014 | Patel et al. | |
| 8,733,611 B2 | 5/2014 | Milliman | |
| 9,038,882 B2* | 5/2015 | Racenet | A61B 17/1155 227/176.1 |
| 9,186,141 B2* | 11/2015 | Williams | A61B 17/072 |
| 9,351,724 B2* | 5/2016 | Penna | A61B 17/068 |
| 9,687,237 B2* | 6/2017 | Schmid | A61B 17/105 |
| 9,782,173 B2* | 10/2017 | Mozdzierz | A61B 17/07292 |
| 10,039,546 B2* | 8/2018 | Williams | A61B 17/1155 |
| 10,213,205 B2* | 2/2019 | Williams | A61B 17/1155 |
| 10,426,470 B2* | 10/2019 | Guerrera | A61B 17/07207 |
| 10,842,495 B2* | 11/2020 | Zhou | A61B 17/1155 |
| 11,065,005 B2* | 7/2021 | Sgroi, Jr. | A61B 17/1155 |
| 11,253,255 B2* | 2/2022 | Eisinger | A61B 17/1155 |
| 11,464,510 B2 | 10/2022 | Valentine et al. | |
| 2003/0111507 A1 | 6/2003 | Nunez | |
| 2004/0073090 A1 | 4/2004 | Butler et al. | |
| 2005/0051597 A1 | 3/2005 | Toledano | |
| 2005/0107813 A1 | 5/2005 | Gilete Garcia | |
| 2006/0000869 A1 | 1/2006 | Fontayne | |
| 2006/0011698 A1 | 1/2006 | Okada et al. | |
| 2006/0201989 A1 | 9/2006 | Ojeda | |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2010/0019016 A1 | 1/2010 | Edoga et al. | |
| 2010/0051668 A1 | 3/2010 | Milliman et al. | |
| 2010/0084453 A1 | 4/2010 | Hu | |
| 2010/0147923 A1 | 6/2010 | D'Agostino et al. | |
| 2010/0163598 A1 | 7/2010 | Belzer | |
| 2010/0224668 A1 | 9/2010 | Fontayne et al. | |
| 2010/0230465 A1 | 9/2010 | Smith et al. | |
| 2010/0258611 A1 | 10/2010 | Smith et al. | |
| 2010/0264195 A1 | 10/2010 | Bettuchi | |
| 2010/0327041 A1 | 12/2010 | Milliman et al. | |
| 2011/0011916 A1 | 1/2011 | Levine | |
| 2011/0114697 A1 | 5/2011 | Baxter, III et al. | |
| 2011/0114700 A1 | 5/2011 | Baxter et al. | |
| 2011/0144640 A1 | 6/2011 | Heinrich et al. | |
| 2011/0147432 A1 | 6/2011 | Heinrich et al. | |
| 2011/0192882 A1 | 8/2011 | Hess et al. | |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0273548 A1 | 11/2012 | Ma et al. | |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |
| 2013/0032628 A1 | 2/2013 | Li et al. | |

(56) References Cited

U.S. PATENT DOCUMENTS

| | | |
|---|---|---|
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2017/0128068 A1 | 5/2017 | Zhang et al. |
| 2018/0125495 A1 * | 5/2018 | Sgroi, Jr. .......... A61B 17/07207 |
| 2018/0317920 A1 * | 11/2018 | Guerrera ............ A61B 17/1155 |

FOREIGN PATENT DOCUMENTS

| | | | |
|---|---|---|---|
| DE | 1057729 B | 5/1959 | |
| DE | 3301713 A1 | 7/1984 | |
| EP | 0152382 A2 | 8/1985 | |
| EP | 0173451 A1 | 3/1986 | |
| EP | 0190022 A2 | 8/1986 | |
| EP | 0282157 A1 | 9/1988 | |
| EP | 0503689 A2 | 9/1992 | |
| EP | 1354560 A2 | 10/2003 | |
| EP | 2138118 A2 | 12/2009 | |
| EP | 2168510 A1 | 3/2010 | |
| EP | 2238926 A2 | 10/2010 | |
| EP | 2524656 A2 | 11/2012 | |
| EP | 2614785 A2 | 7/2013 | |
| EP | 2623042 A2 | 8/2013 | |
| EP | 2754398 A2 | 7/2014 | |
| EP | 2823774 A2 | 1/2015 | |
| EP | 3378411 A1 * | 9/2018 | ........... A61B 17/068 |
| EP | 3649966 A1 | 5/2020 | |
| EP | 3730067 A1 | 10/2020 | |
| FR | 1136020 A | 5/1957 | |
| FR | 1461464 A | 2/1966 | |
| FR | 1588250 A | 4/1970 | |
| FR | 2443239 A1 | 7/1980 | |
| GB | 1185292 A | 3/1970 | |
| GB | 2016991 A | 9/1979 | |
| GB | 2070499 A | 9/1981 | |
| JP | 2004147969 A | 5/2004 | |
| JP | 2013138860 A | 7/2013 | |
| JP | 2018158108 A | 10/2018 | |
| NL | 7711347 A | 4/1979 | |
| SU | 1509052 A1 | 9/1989 | |
| WO | 8706448 A1 | 11/1987 | |
| WO | 8900406 A1 | 1/1989 | |
| WO | 9006085 A1 | 6/1990 | |
| WO | 9835614 A1 | 8/1998 | |
| WO | 0154594 A1 | 8/2001 | |
| WO | 2008107918 A1 | 9/2008 | |

OTHER PUBLICATIONS

Extended European Search Report dated Mar. 2, 2021, issued in corresponding European Appl. No. 20187607, 13 pages.

Japanese Notice of Allowance dated Feb. 26, 2024, issued in corresponding JP Appln. No. 2020114959, 3 pages. [English Translation Not Available].

* cited by examiner

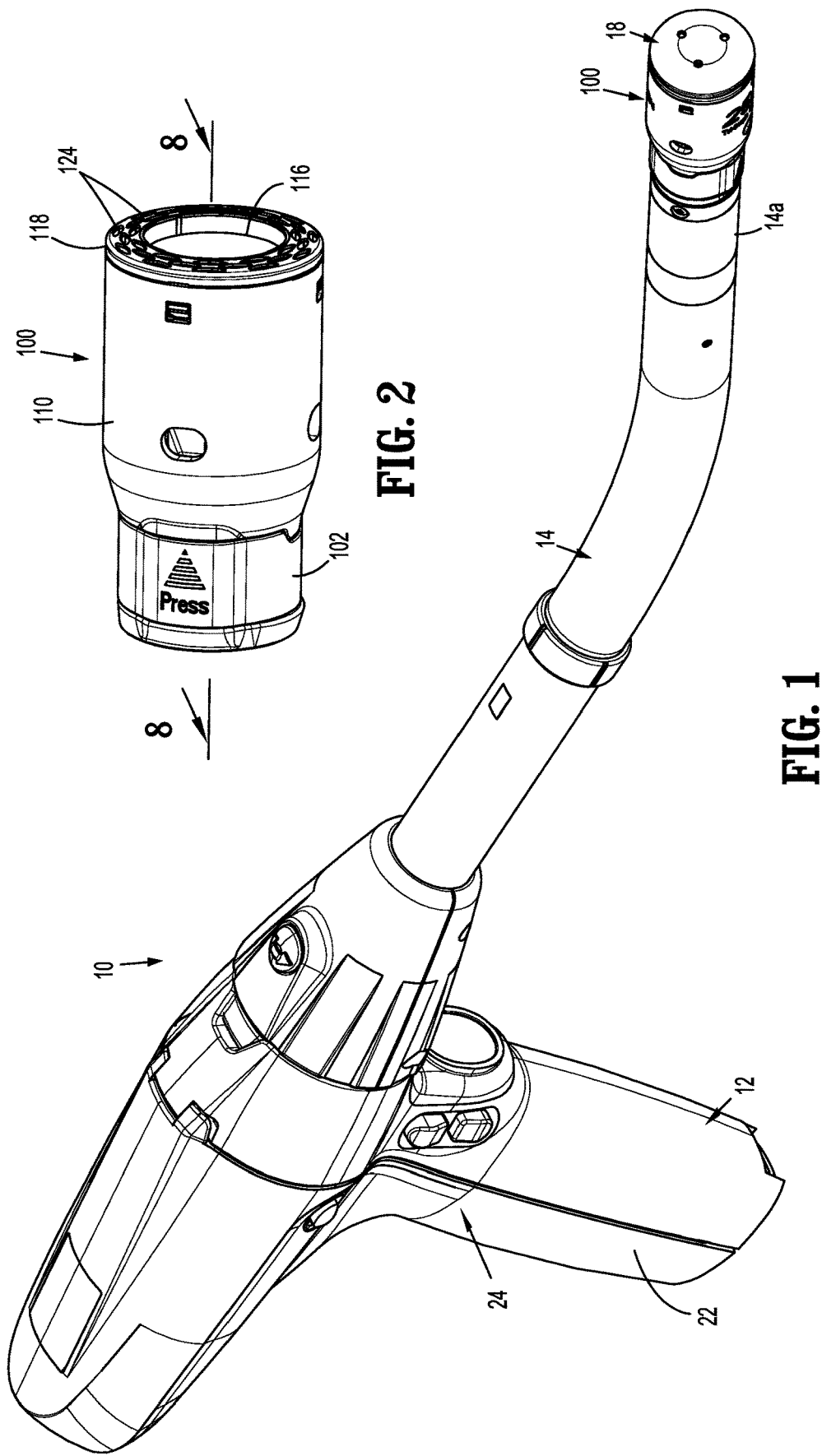

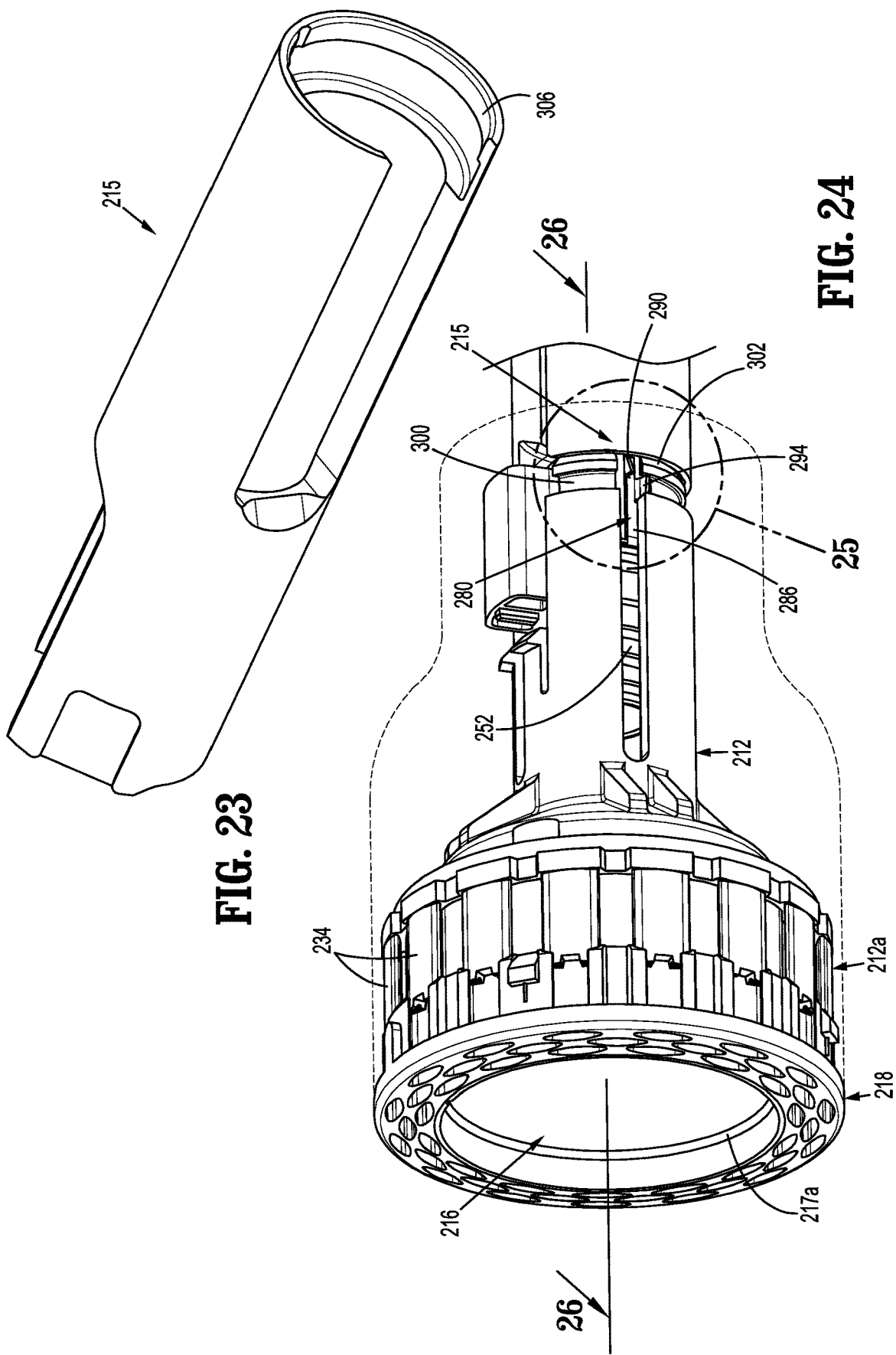

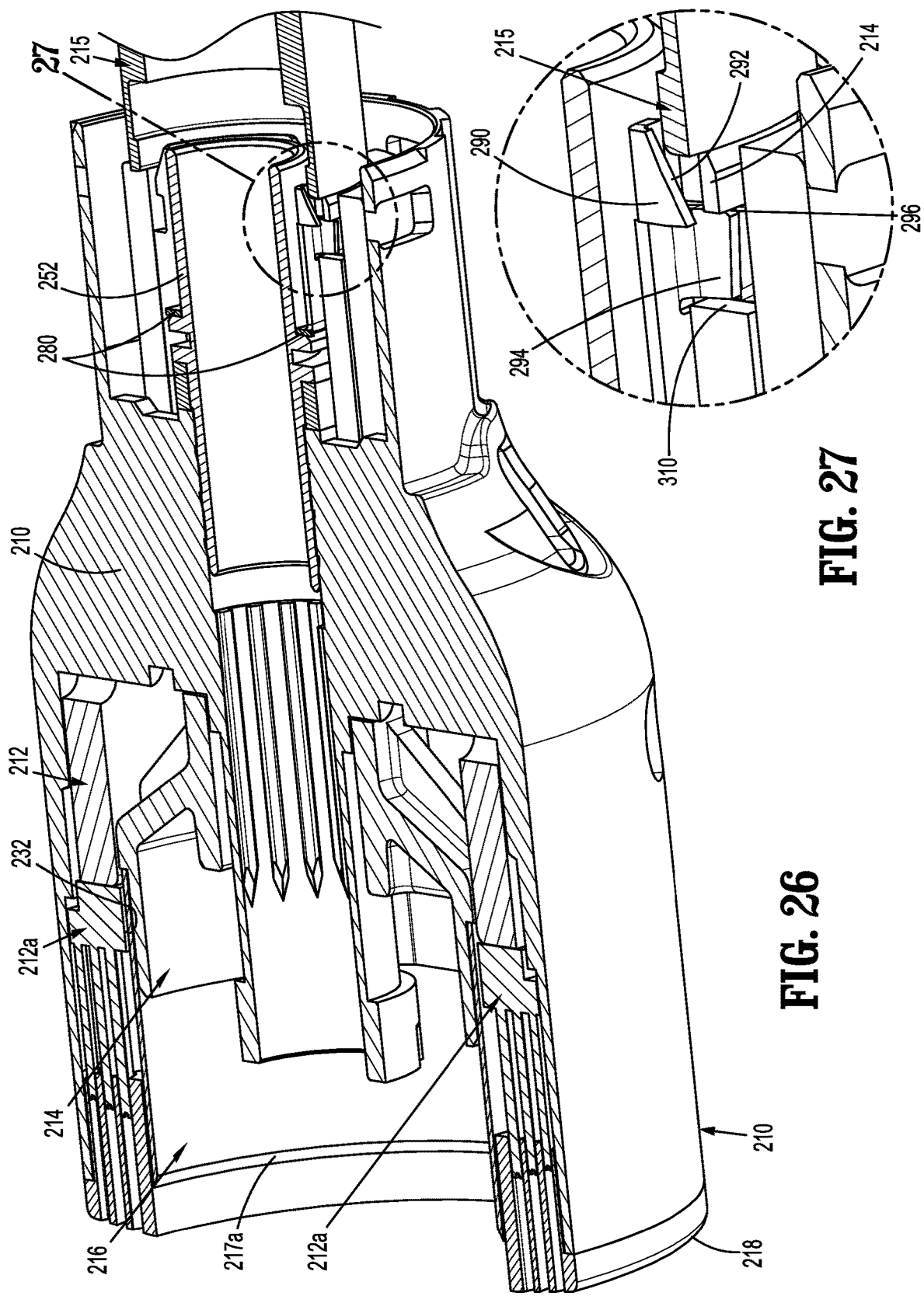

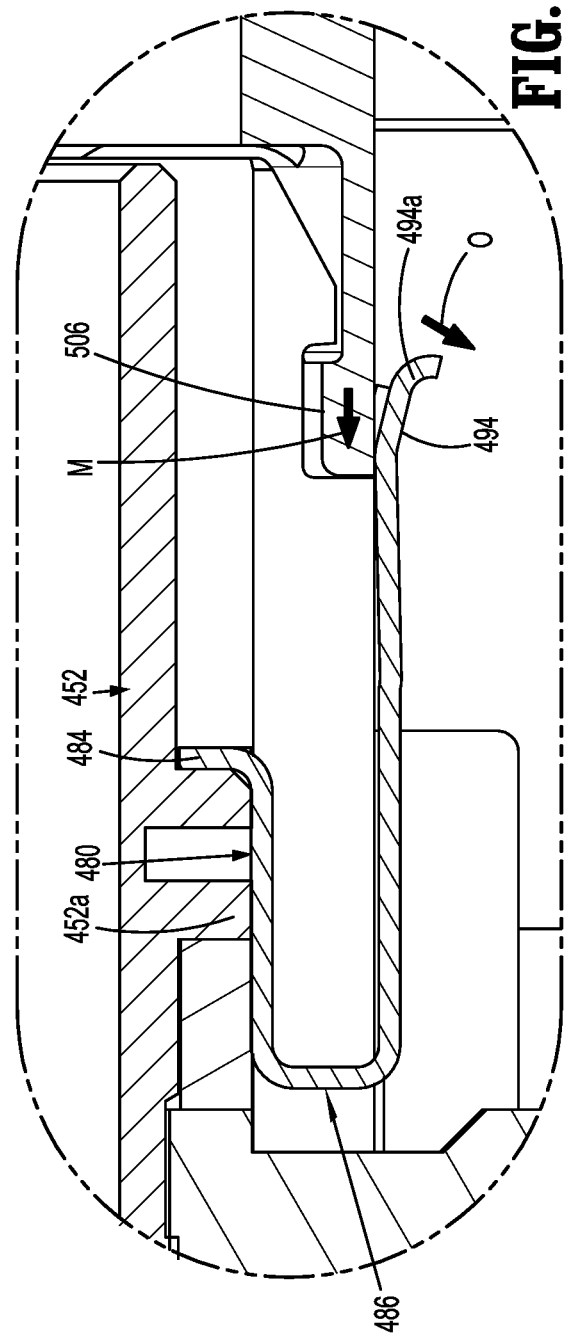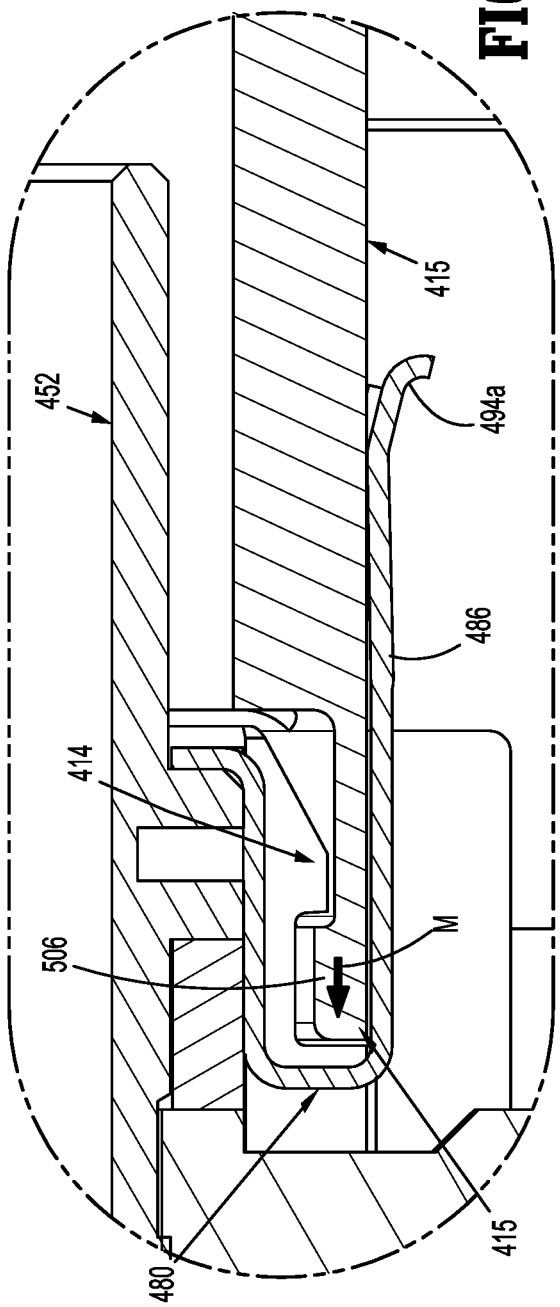

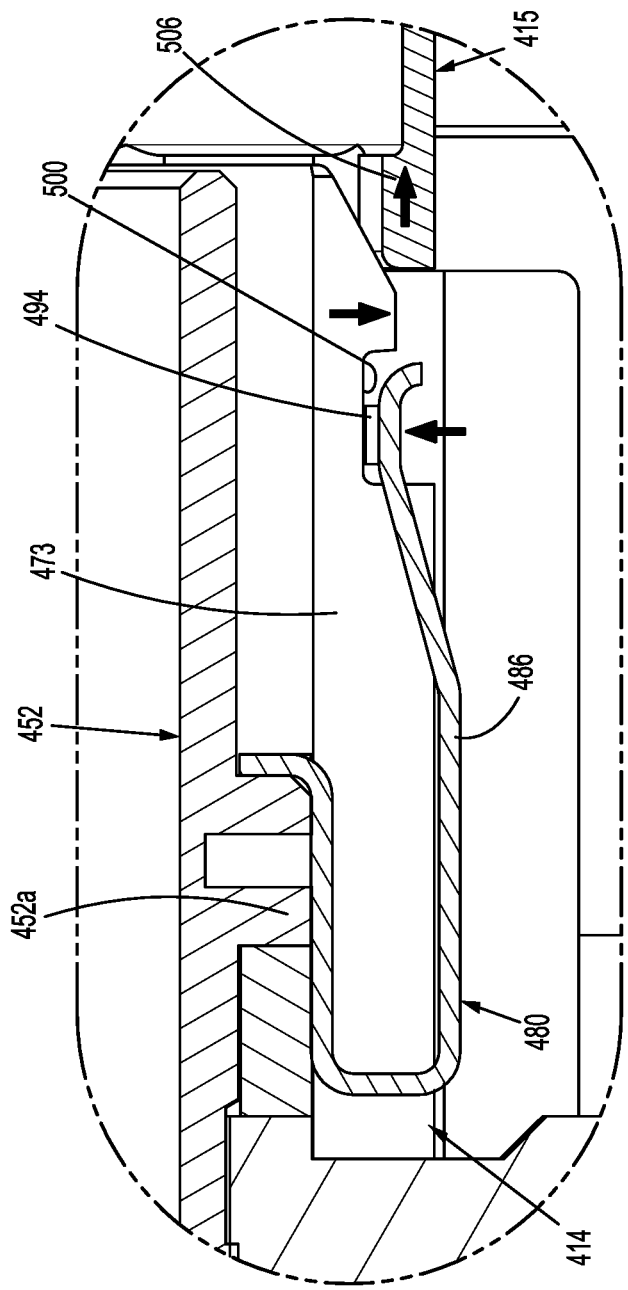

RELOAD ASSEMBLY WITH KNIFE CARRIER LOCKOUT

CROSS-REFERENCE TO RELATED APPLICATIONS

This application is a divisional application of U.S. application Ser. No. 16/890,334, filed Jun. 2, 2020, which claims the benefit of and priority to U.S. Provisional Application Ser. No. 62/878,789, filed Jul. 26, 2019, the entire disclosure of each of which are incorporated by reference herein.

FIELD

The disclosure is directed to circular stapling devices and, more particularly, to reload assemblies for circular stapling devices with structure to retain a knife carrier of the reload assembly in a retracted position after the stapling device is fired.

BACKGROUND

Conventional circular stapling devices include an elongate body and a shell or reload assembly that is supported on a distal portion of the elongate body. The reload assembly includes a shell housing, a staple cartridge having a plurality of staples supported on the shell housing, a pusher assembly, a knife defining a cylindrical cavity, and a knife carrier that supports the knife. The pusher assembly includes an annular pusher and a staple pushing member that is engaged with the annular pusher and is movable to move the staple pushing member to eject staples from the staple cartridge. The knife carrier is movable to advance the knife through the staple cartridge to core or cut tissue.

After a stapling device has been operated to staple and cut tissue, the knife carrier and the knife are retracted to withdraw the knife into the shell housing. This serves two purposes. The first purpose is to move the knife to a position to allow removal of a tissue donut from within the cavity defined by the knife. The second purpose is to position the knife in a location recessed within the shell housing to avoid injury to a clinician during manipulation and disposal of the reload assembly.

In some instances, the tissue donut is compressed within the cavity defined by the knife to such a degree that removal of the tissue donut from within the cavity defined by the knife is difficult. A continuing need exists in the art for a reload assembly that includes improved structure for retaining the knife/knife carrier in a retracted position.

SUMMARY

One aspect of the disclosure is directed to a surgical stapling device including an adaptor assembly and a reload assembly. The adaptor assembly has a proximal end portion and a distal end portion. The reload assembly is supported on the distal end portion of the adaptor assembly and includes a shell housing, a staple pusher, a staple actuator, a knife carrier, and a knife supported on the knife carrier. The shell housing includes an outer housing portion and an inner housing portion that together define an annular cavity. The staple cartridge supports a plurality of staples. The staple pusher is supported within the annular cavity and is movable from a retracted position to an advanced position to eject staples from the staple cartridge. The staple actuator is supported within the annular cavity and has a stop surface. The staple actuator is engaged with the staple pusher and is movable from a retracted position to an advanced position to move the staple pusher from its retracted position to its advanced position. The staple actuator and the staple pusher define a through bore. The knife carrier is supported within the through bore and is movable between a retracted position and an advanced position. The knife carrier supports a resilient locking member that is aligned with the stop surface on the staple actuator when the staple actuator is in its advanced position and the knife carrier is in its retracted position to prevent readvancement of the knife carrier.

In embodiments, the stapling device includes a handle assembly, wherein the proximal end portion of the adaptor assembly is supported on the handle assembly.

In some embodiments, the locking member is movable from an undeformed state in which the locking member extends outwardly and distally from the knife carrier to a deformed state in which the locking member is substantially aligned with a longitudinal axis of the knife carrier.

In certain embodiments, the locking member is positioned distally of the stop surface of the staple actuator when the staple actuator and the knife carrier are in their retracted positions, wherein the locking member is movable from the undeformed state to the deformed state to allow the locking member to pass proximally by the staple actuator when the staple actuator is in its advanced position and the knife carrier is moved from its advanced position to its retracted position.

In embodiments, the knife carrier includes a hook member that is aligned with the stop surface such that movement of the knife carrier from its retracted position to its advanced position moves the staple actuator from its retracted position to its advanced position.

In some embodiments, the locking member is supported on the knife carrier in cantilevered fashion.

In certain embodiments, the locking member is formed from a flat leaf spring.

In embodiments, the locking member is formed from wire having a cylindrical cross-section.

Another aspect of the disclosure is directed to a surgical stapling device that includes an adaptor assembly and a reload assembly. The adaptor assembly includes a proximal end portion, a distal end portion, and a knife driver. The knife driver is movable between a retracted position and an advance position. The reload assembly is supported on the distal end portion of the adaptor assembly and includes a shell housing, a staple cartridge, a staple pusher, a staple actuator, a knife carrier supporting a knife, and a locking member. The shell housing includes an outer housing portion and an inner housing portion that define an annular cavity. The staple cartridge is supported on the shell housing and includes a plurality of staples. The staple pusher is supported within the annular cavity and is movable from a retracted position to an advanced position to eject staples from the staple cartridge. The staple actuator is supported within the annular cavity in a position to engage the staple pusher and defines a through bore. The staple actuator is movable from a retracted position to an advanced position to move the staple pusher from its retracted position to its advanced position. The knife carrier is supported within the through bore and includes a distal portion and a proximal portion. The knife carrier is movable between a retracted position and an advanced position in response to movement of the knife driver from its retracted position to its advanced position. The locking member is supported on the inner housing portion and includes a lockout latch that is movable from an undeformed state to a deformed state in response to movement of the knife driver from its retracted position towards its advanced position. In the undeformed state, the lockout latch is engaged with the knife carrier to prevent advancement of the knife carrier within the shell housing.

In embodiments, the proximal portion of the knife carrier includes resilient longitudinal body portions that define an annular recess, and the knife driver has a distal end portion including an annular rib, wherein the annular rib being received within the annular recesses to couple the knife driver to the knife carrier when the knife driver is moved from its retracted position towards its advanced position.

In some embodiments, the lockout latch supports a first tab and the knife carrier defines a notch, wherein the first tab being received within the notch when the lockout latch is in its undeformed state to prevent advancement of the knife carrier within the shell housing.

In certain embodiments, the lockout latch includes a second tab having an angled proximally facing surface, and the knife driver is movable from its retracted position towards its advanced position into engagement with the second tab to move the lockout latch from the undeformed state to the deformed state.

In embodiments, the proximal end portion of each of the longitudinal body portions includes a tapered surface that is positioned proximally of the annular recesses, wherein the tapered surfaces are aligned with and positioned distally of the distal end portion of the knife driver when the knife driver and the knife carrier are in their retracted positions.

In some embodiments, a bushing is supported on the inner housing portion of the shell housing and the locking member is supported on the bushing.

In certain embodiments, the bushing includes a protrusion and the locking member includes an annular ring defining a cutout, wherein the annular ring is received about the bushing and the protrusion is received within the cutout to prevent the locking member from rotating in relation to the bushing.

In embodiments, the locking member includes an annular ring supported on the bushing, and the lockout latch of the locking member includes a transverse portion and a proximally extending longitudinal portion that extends from the transverse portion in cantilevered fashion.

In some embodiments, the transverse portion of the lockout latch extends through a slot defined by the longitudinal body portions of the knife carrier and the proximally extending longitudinal portion of the lockout latch supports a latch member that is positioned within one of the annular recesses of one of the longitudinal body portions of the knife carrier when the lockout latch is in the undeformed state to obstruct distal movement of the knife carrier within the shell housing.

In certain embodiments, the locking member includes a cam surface that is positioned adjacent to the latch member to be engaged by the distal end portion of the knife driver when the knife driver is moved from its retracted position towards its advanced position to move the locking member from the undeformed state to the deformed state.

Another aspect of the disclosure is directed to a reload assembly including a shell housing, a staple cartridge, a staple pusher, a staple actuator, a knife carrier, and a locking member. The shell housing includes an outer housing portion and an inner housing portion that define an annular cavity. The staple cartridge is supported on the shell housing and includes a plurality of staples. The staple pusher is supported within the annular cavity and is movable from a retracted position to an advanced position to eject staples from the staple cartridge. The staple actuator is supported within the annular cavity in a position to engage the staple pusher and defines a through bore. The staple actuator is movable from a retracted position to an advanced position to move the staple pusher from its retracted position to its advanced position. The knife carrier is supported within the through bore and includes a distal portion and a proximal portion. The knife carrier supports a knife and is movable between a retracted position and an advanced position. The locking member is supported on the inner housing portion and includes a lockout latch that is movable from an undeformed state to a deformed state in response to firing of a surgical stapling device, wherein in the undeformed state, the lockout latch is engaged with the knife carrier to prevent advancement of the knife carrier within the shell housing.

Other features of the disclosure will be appreciated from the following description.

BRIEF DESCRIPTION OF THE DRAWINGS

Various embodiments of the disclosed reload assembly for a surgical stapling device are described herein below with reference to the drawings, wherein:

FIG. 1 is a side perspective view of a surgical stapling device including an exemplary embodiment of the disclosed reload assembly with the stapling device in a clamped position;

FIG. 2 is a side perspective view of the reload assembly of the stapling device shown in FIG. 1;

FIG. 23 is an enlarged view of the indicated area of detail shown in FIG. 14;

FIG. 24 is a side perspective view of the reload assembly shown in FIG. 14 assembled with a shell housing shown in phantom and the staple actuator and knife carrier in retracted positions;

FIG. 26 is a cross-sectional view taken along section line 26-26 of FIG. 4 with the reload assembly in a pre-fired state;

FIG. 27 is an enlarged view of the indicated area of detail shown in FIG. 26;

FIG. 40 is an enlarged view of the indicated area of detail shown in FIG. 35 with the knife carrier driver coupled to the knife carrier and the locking member retained in its unlatched position;

FIG. 41 is an enlarged view of the indicated area of detail shown in FIG. 35 with the knife carrier driver coupled to the knife carrier and the locking member retained in its unlatched state as the knife carrier driver and knife carrier are moved towards their advanced positions to cut tissue; and FIG. 42 is an enlarged view of the indicated area of detail shown in FIG. 35 with the knife carrier driver returned to its retracted position after firing of the stapling device, with the knife carrier driver uncoupled from the knife carrier and the locking member in its latched state.

DETAILED DESCRIPTION

Figure 3:
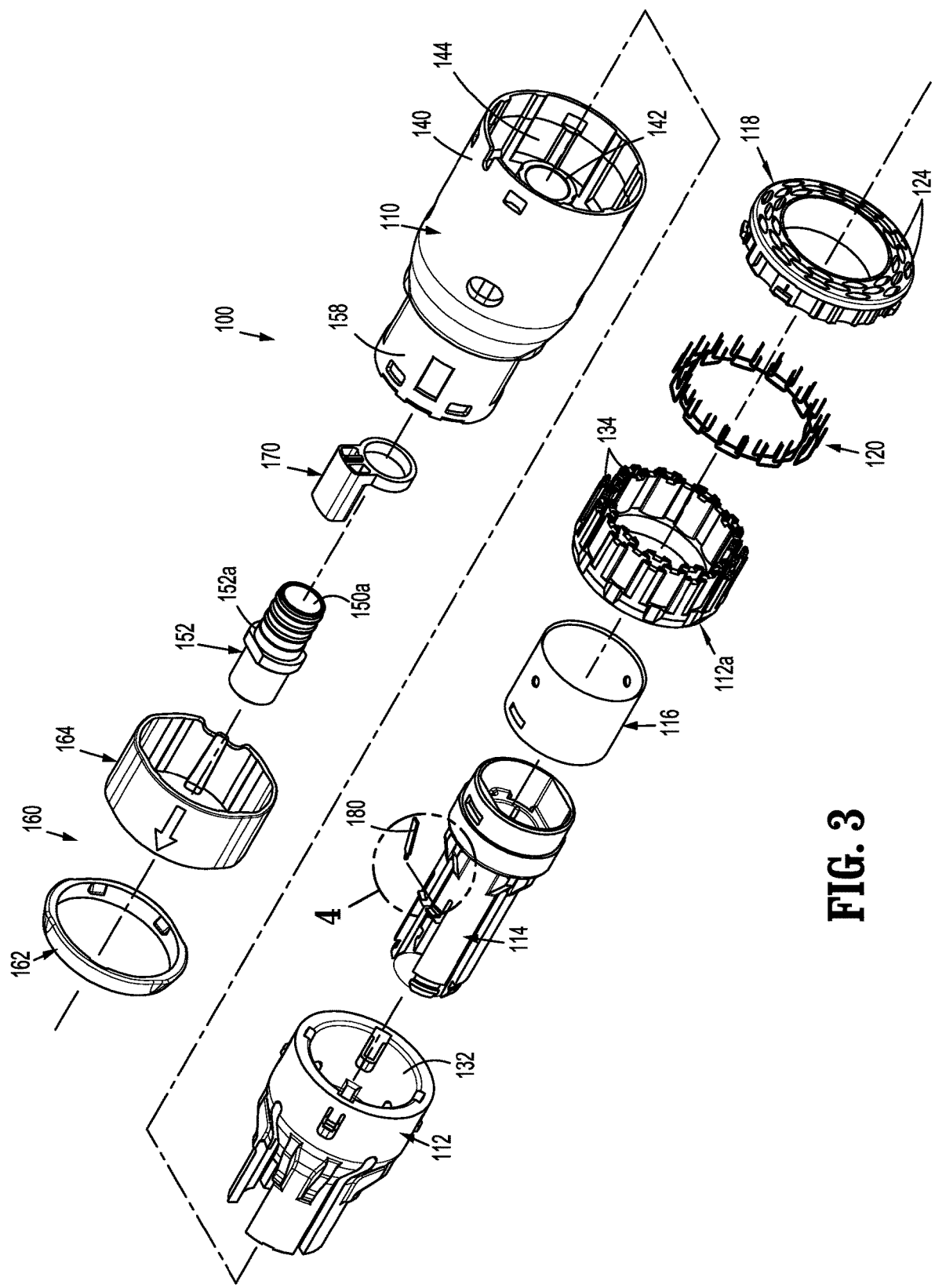
FIG. 3 is a side perspective exploded view of the reload assembly shown in FIG. 2.
Figure 4:
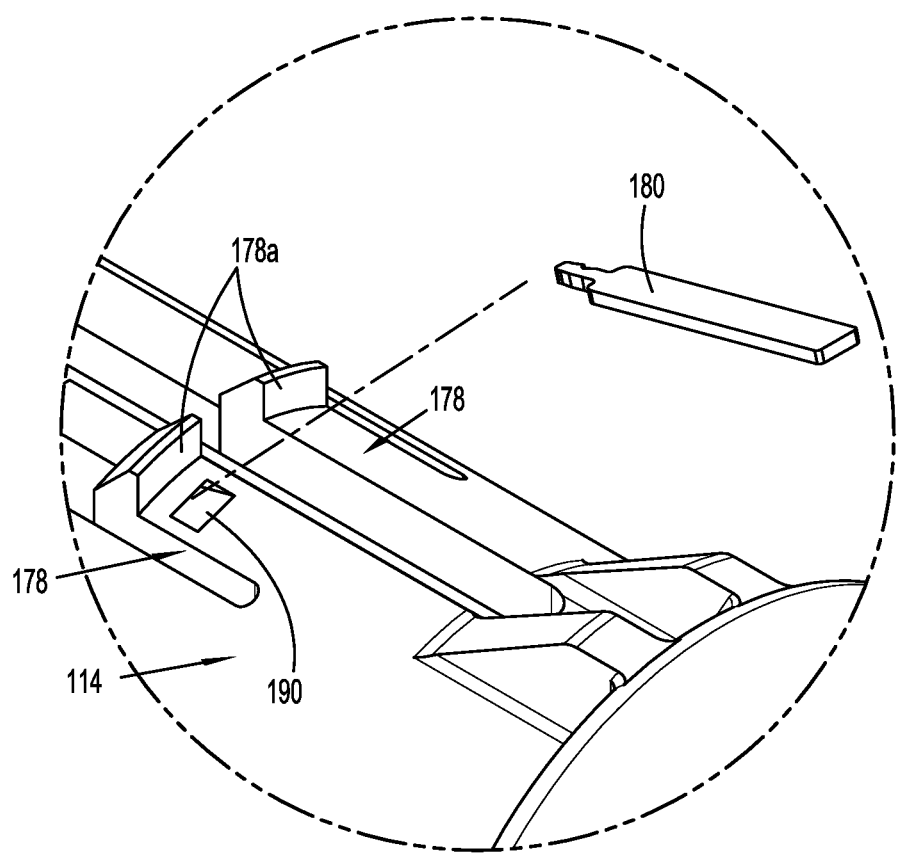
FIG. 4 is an enlarged view of the indicated area of detail shown in FIG. 3.
Figure 5:
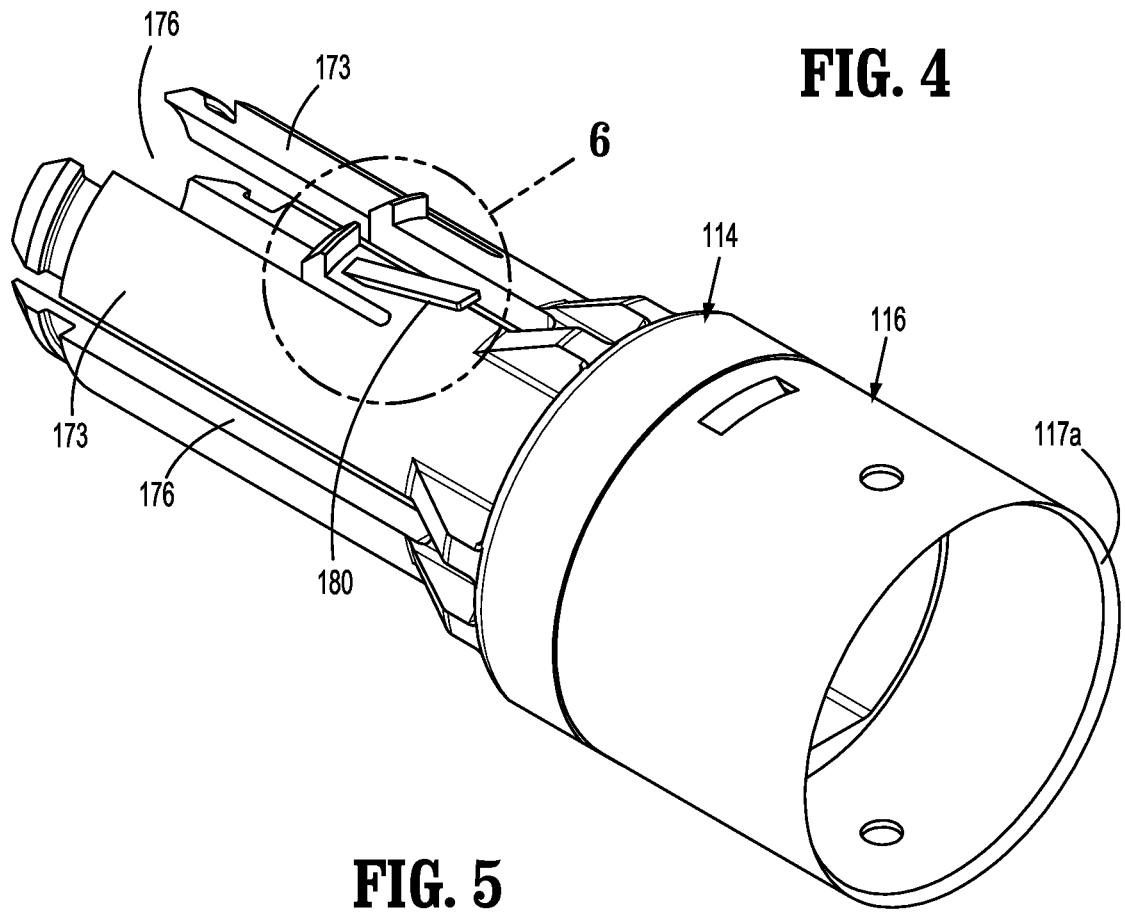
FIG. 5 is a side perspective view from the distal end of a knife carrier of the reload assembly shown in FIG. 3.
Figure 6:
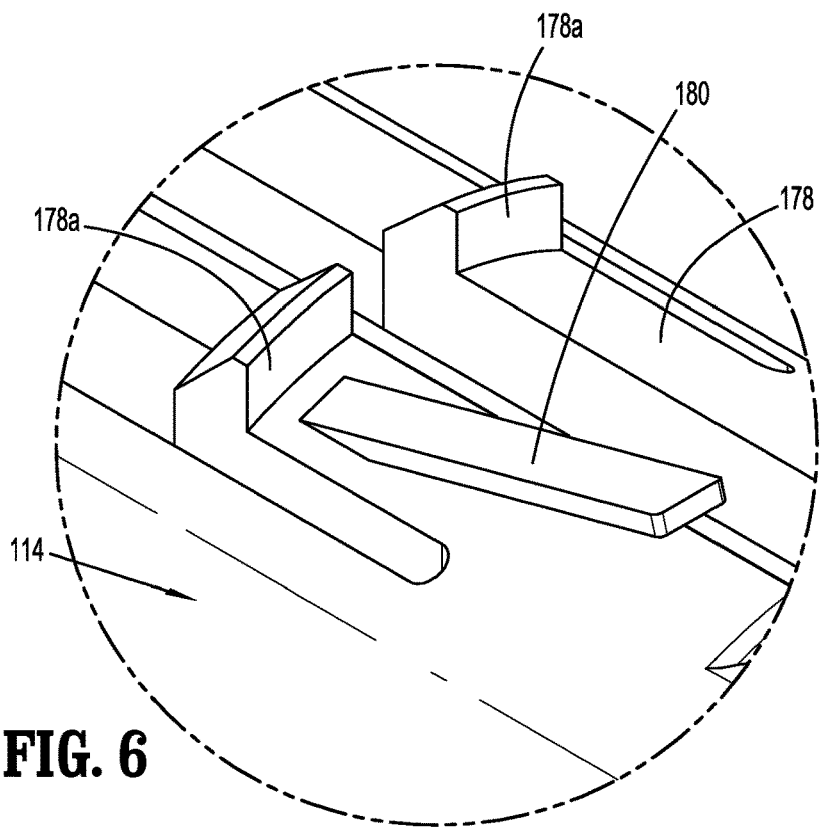
FIG. 6 is an enlarged view of the indicated area of detail shown in FIG. 5.

The disclosed reload assembly for a surgical stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

FIGS. 1 and 2 illustrate a circular stapling device 10 including an exemplary embodiment of the disclosed reload assembly shown generally as reload assembly 100. The stapling device 10 includes a handle assembly 12, an elongate body or adaptor assembly 14, the reload assembly 100, and an anvil assembly 18 that is supported for movement in relation to the reload assembly 100 between spaced and approximated positions as is known in the art. In embodiments, the reload assembly 100 includes a proximal portion 102 that is releasably coupled to a distal portion 14a of the elongate body 14. In some embodiments, the handle assembly 12 includes a stationary grip 22 that supports actuation buttons 24 for controlling operation of various functions of the stapling device 10 including approximation of the reload and anvil assemblies 100 and 18, respectively, firing of staples from the reload assembly 100, and cutting or coring of tissue.

The stapling device 10 is illustrated as an electrically powered stapling device including an electrically powered handle assembly 12 that may support one or more batteries (not shown). The elongate body 14 is in the form of an adaptor assembly that translates power from the handle assembly 12 to the reload and anvil assemblies 100, 18, respectively. Examples of electrically powered stapling devices can be found in U.S. Pat. Nos. 9,055,943, 9,023,014, and U.S. Publication Nos. 2018/0125495, and 2017/0340351. Alternately, it is envisioned that the reload assembly could also be incorporated into a manually powered stapling device such as disclosed in U.S. Pat. No. 7,303,106 (the '106 Patent) or a stapling device that is configured for use with a robotic system such as disclosed in U.S. Pat. No. 9,962,159 that does not include a handle assembly.

Figure 8:
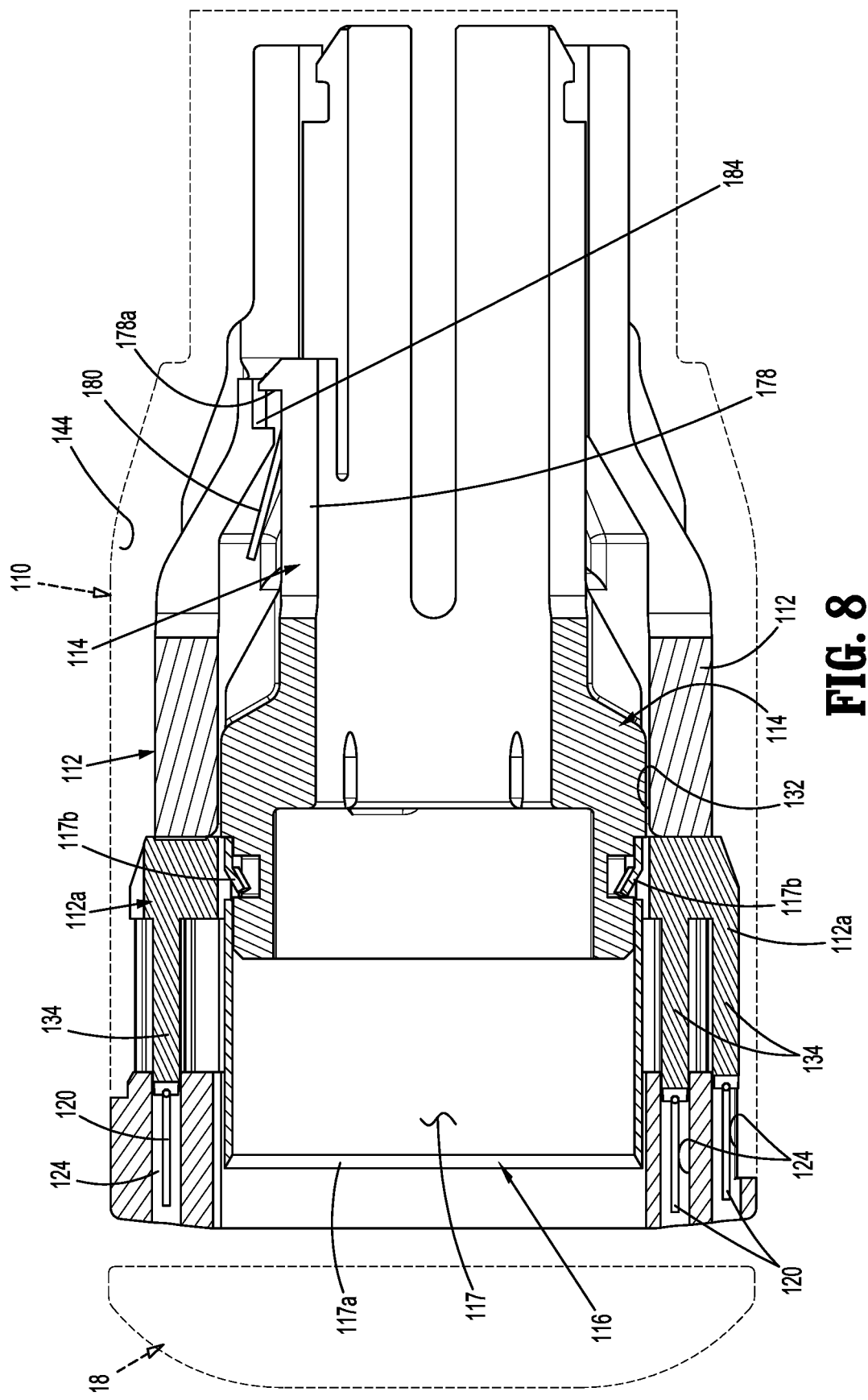
FIG. 8 is a cross-sectional view taken along section line 8-8 of FIG. 2 with the reload assembly in a pre-fired state.

FIGS. 2 and 3 illustrate the reload assembly 100 which includes a shell housing 110, a staple actuator 112, a staple pushing member 112a, a knife carrier 114, an annular knife 116 supported on the knife carrier 114, a staple cartridge 118, and a plurality of staples 120 supported within the staple cartridge 118. The staple cartridge 118 is annular and defines annular rows of staple pockets 124. Each of the staple pockets 124 supports one staple of the plurality of staples 120. The staple actuator 112 and the staple pushing member 112a together define a longitudinal through bore 132 (FIG. 8). The staple actuator 112 has a distal portion that abuts a proximal portion of the staple pushing member 112a such that distal movement of the staple actuator 112 within the shell housing 110 causes distal movement of the staple pushing member 112a within the shell housing 110. The staple pushing member 112a of the reload assembly 100 has a plurality of fingers 134. Each of the plurality of fingers 134 is received within a respective one of the staple pockets 124 of the staple cartridge 118 and is movable through the respective staple pocket 124 to eject the staples 120 from the staple pockets 124 when the staple pushing member 112a is moved from a retracted position to an advanced position within the shell housing 110.

The shell housing 110 includes an outer housing portion 140 and an inner housing portion 142 that are spaced from each other to define an annular cavity 144 (FIG. 3) between the outer and inner housing portions 140 and 142. The staple actuator 112 and the staple pushing member 112a are movable within the annular cavity 144 of the shell housing 110 from retracted positions to advanced positions to eject the staples 120 from the staple cartridge 118.

The annular knife 116 is supported about an outer surface of the knife carrier 114, defines a cylindrical cavity 117, and includes a distal cutting edge 117a. In embodiments, the annular knife 116 includes inwardly extending tangs 117b that are received within pockets 114a defined in an outer surface of the knife carrier 114 to secure the annular knife 116 to the knife carrier 114. The knife carrier 114 and annular knife 116 are positioned within the through bore 132 of the staple actuator 112 and are movable from retracted positions to advanced positions to cut tissue positioned radially inward of the staple cartridge 118.

The inner housing portion 142 of the shell housing 110 defines a through bore 150 (FIG. 3) that receives an anvil shaft (not shown) of the anvil assembly 18. For a more detailed description of an exemplary anvil assembly 18, see, e.g., the '106 Patent. The through bore 150 has a proximal portion that receives a bushing 152 (FIG. 3) that defines a through bore 150a that is coaxial and forms an extension of the through bore 150 of the inner housing portion 142. In embodiments, the bushing 152 is formed of a high strength material, e.g., metal, to provide added strength to the inner housing portion 142 of the shell housing 110 and includes an annular flange 152a.

The shell housing 110 includes a proximal portion 158 (FIG. 3) that supports a coupling mechanism 160 (FIG. 2) that is operable to releasably couple the reload assembly 100 to the adaptor assembly 14 of the stapling device 10 (FIG. 1). The coupling mechanism 160 allows for removal and replacement of the reload assembly 100 to facilitate reuse of the stapling device 10. The coupling mechanism 160 includes a retaining member 162 and a coupling member 164. The coupling member 164 is received about the proximal portion 158 (FIG. 3) of the shell housing 110 and is configured to engage the distal portion 14a (FIG. 1) of the adaptor assembly 14 to couple the reload assembly 100 to the adaptor assembly 14. It is envisioned that other coupling mechanisms can be used to secure the reload assembly 100 to the adaptor assembly 14. Alternately, the reload assembly 100 can be non-removably secured to the adaptor assembly 14.

The reload assembly 100 may include an e-prom holder 170 (FIG. 3) that is supported on the shell housing 110 and is configured to support an e-prom (not shown). As is known in the art, an e-prom can communicate with the adaptor assembly 14 to provide information to the adaptor assembly 14 and the handle assembly 12 regarding characteristics of the reload assembly 10. In some embodiments, the e-prom holder 70, may define a cylindrical collar that is received about a distal portion of the bushing 52.

Figure 9:
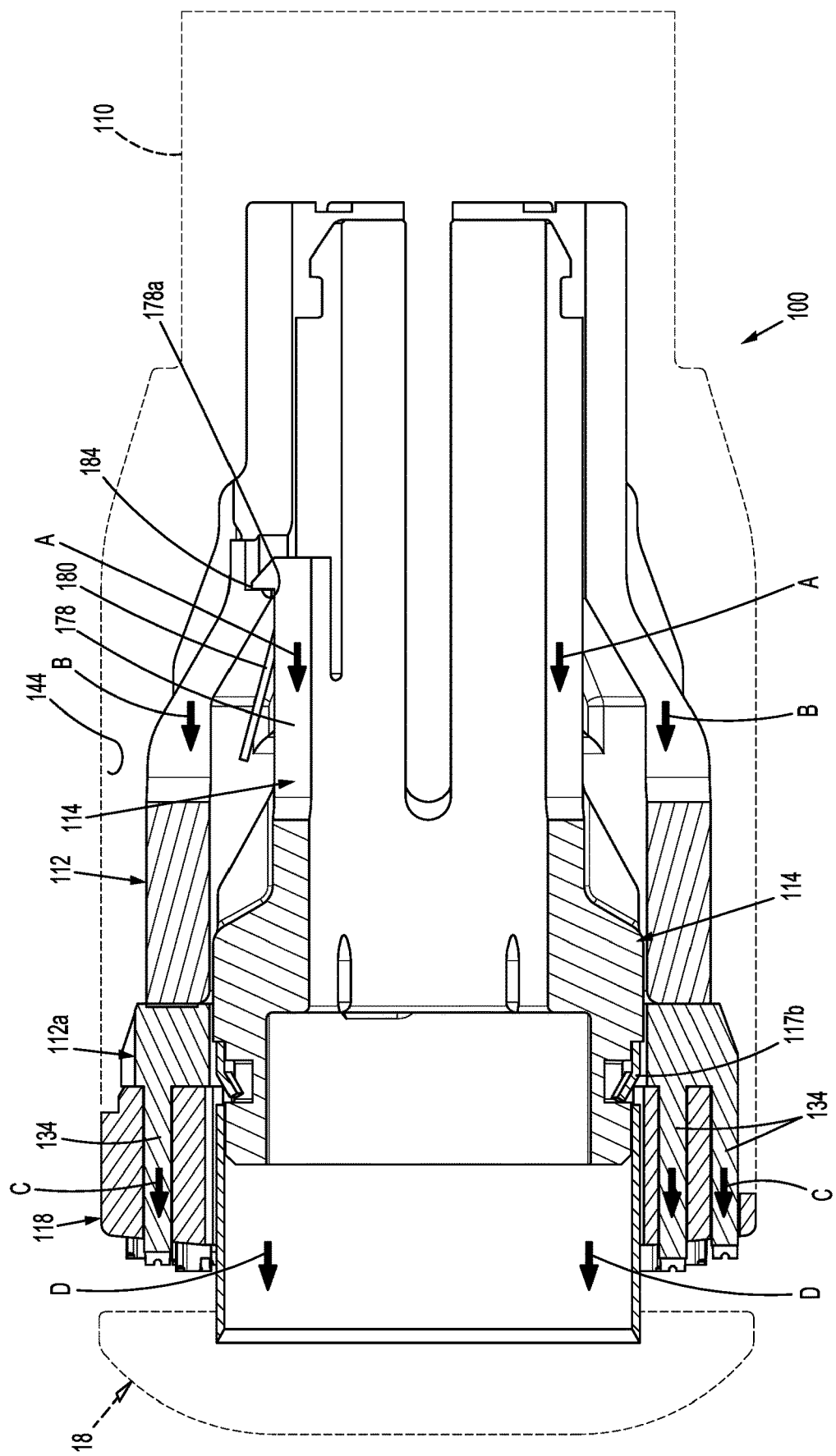
FIG. 9 is a cross-sectional view taken along section line 8-8 of FIG. 2 with the reload assembly in a fired state and the knife carrier in an advanced position.

FIGS. 3-6 illustrate the knife carrier 114 which includes a plurality of spaced resilient longitudinal body portions 173 that are spaced from each other and together define a central bore 172. The central bore 172 of the knife carrier 114 receives the inner housing portion 142 of the shell housing 110 such that the knife carrier 114 is movable about the inner housing portion 142 of the shell housing 110 between a retracted position (FIG. 8) and an advanced position (FIG. 9). The longitudinal body portions 173 of the knife carrier 114 define slots 176 that receive guide portions (not shown) of the shell housing 110 to limit the knife carrier 114 to longitudinal movement within the shell housing 110. In embodiments, the knife carrier 114 includes hook members 178 that are positioned to engage the staple actuator 112 to move the staple actuator 112 from its retracted position to its advanced position. The hook members 178 extend radially outwardly from the knife carrier 114 towards the staple actuator 112 within the annular cavity 144 (FIG. 3) of the shell housing 110. Each of the hook members 178 includes an engagement surface 178a and supports a locking member 180. In embodiments, the locking members 180 are positioned distally of the engagement surfaces 178a of the hook members 178 and extend outwardly and distally from the knife carrier 114 towards the staple actuator 112 at an acute angle. The locking members 180 may be formed of a resilient material that can be deformed inwardly via engagement with staple actuator 112 towards an outer surface of the knife carrier 114 but is sufficiently rigid to prevent readvancement of the knife carrier 114 as described below.

Figure 7:
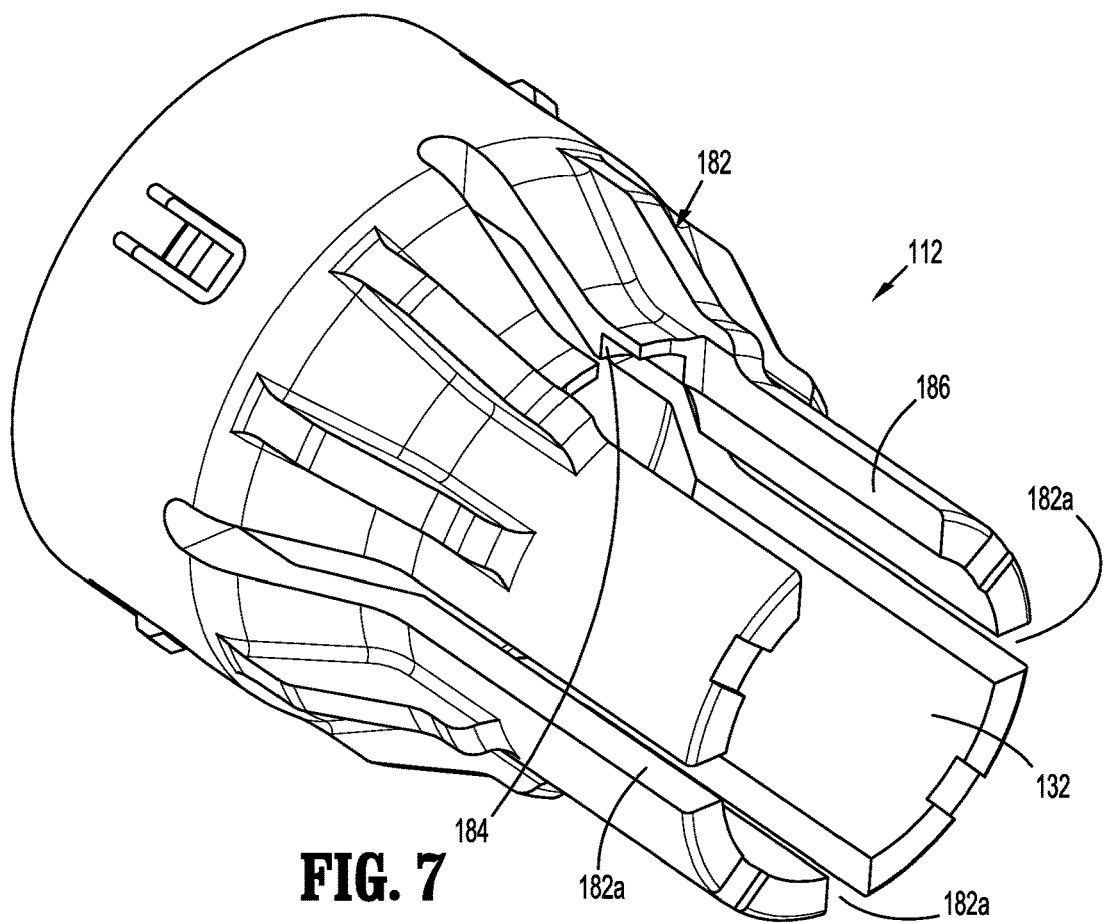
FIG. 7 is a side perspective view from the proximal end of a staple actuator of the reload assembly shown in FIG. 3.

FIG. 7 illustrates the staple actuator 112 which includes a body 182 that is also received about the inner housing portion 142 (FIG. 3) of the shell housing 110 and is movable from a retracted position (FIG. 8) to an advanced position (FIG. 9) in response to movement of the knife carrier 114 from its retracted position to its advanced position. The body 182 defines a plurality of guide slots 182a and at least one stop surface 184. In some embodiments, the at least one stop surface 184 is positioned at a distal end of a channel 186 formed in the body 182. The channel 186 is positioned to receive the hook members 178. The guide slots 182a of the staple actuator 112 receive the guide members (not shown) of the shell housing 110 to limit the staple actuator 112 to longitudinal movement within the shell housing 110. The at least one stop surface 184 of the staple actuator 112 is longitudinally aligned with the engagement surfaces 178a of the hook members 178 (FIG. 4) of the knife carrier 114 such that advancement of the knife carrier 114 within the through bore 132 of the staple actuator 112 causes the engagement surfaces 178a of the hook members 178 of the knife carrier 112 to engage the at least one stop surface 184 of the staple actuator 112 to advance the staple actuator 112 within the shell housing 110 from its retraced position to its advanced position.

FIG. 8 illustrates the reload assembly 100 in a pre-fired condition with the knife carrier 114 and staple actuator 112 of the reload assembly 100 (FIG. 3) in retracted positions and the locking member 180 in an unlatched position located distally of the at least one stop surface 184 of the staple actuator 112. When the knife carrier 114 and the staple actuator 112 are in pre-fired retracted positions, the engagement surface 178a of each of the hook members 178 is aligned with and spaced proximally of the respective stop surface 184 of the staple actuator 112 and each of the locking members 180 is positioned distally of a respective stop surface 184 and is in an undeformed state.

FIG. 9 illustrates the reload assembly 100 as the staple actuator 112 and the knife carrier 114 are moved to their advanced positions. As the knife carrier 114 is moved distally within the shell housing 110 to its advanced position by a knife carrier driver (not shown) of the stapling device 10 (FIG. 1) in the direction indicated by arrows "A", the engagement surfaces 178a of the hook members 178 engage the stop surfaces 184 of the staple actuator 112 such that the staple actuator 112 is moved distally with the knife carrier 114 in the direction indicated by arrows "B". As the staple actuator 112 moves distally within the shell housing 110, the staple pushing member 112a is moved distally in the direction indicated by arrows "C" to advance the plurality of fingers 134 of the staple pushing member 112a through the staple pockets 124 of the staple cartridge 118 to eject the staples 120 from the staple cartridge 118 into the anvil assembly 18. As illustrated, the annular knife 116 which is secured to the knife carrier 114 is moved distally with the knife carrier 114 in the direction indicated by arrows "D" to cut tissue.

Figure 10:
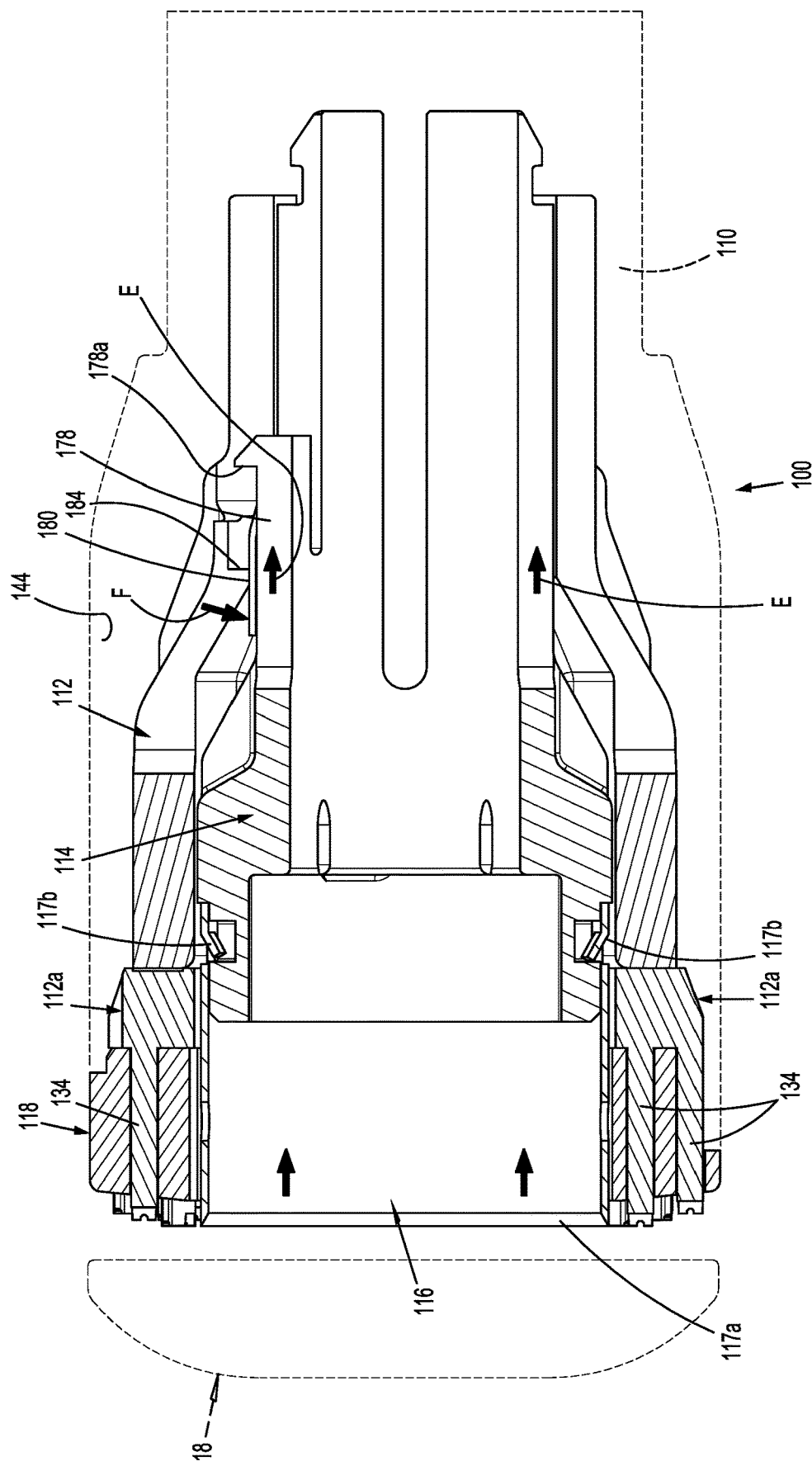
FIG. 10 is a cross-sectional view taken along section line 8-8 of FIG. 2 with the reload assembly in a fired state and the knife carrier moving toward its retracted position.
Figure 11:
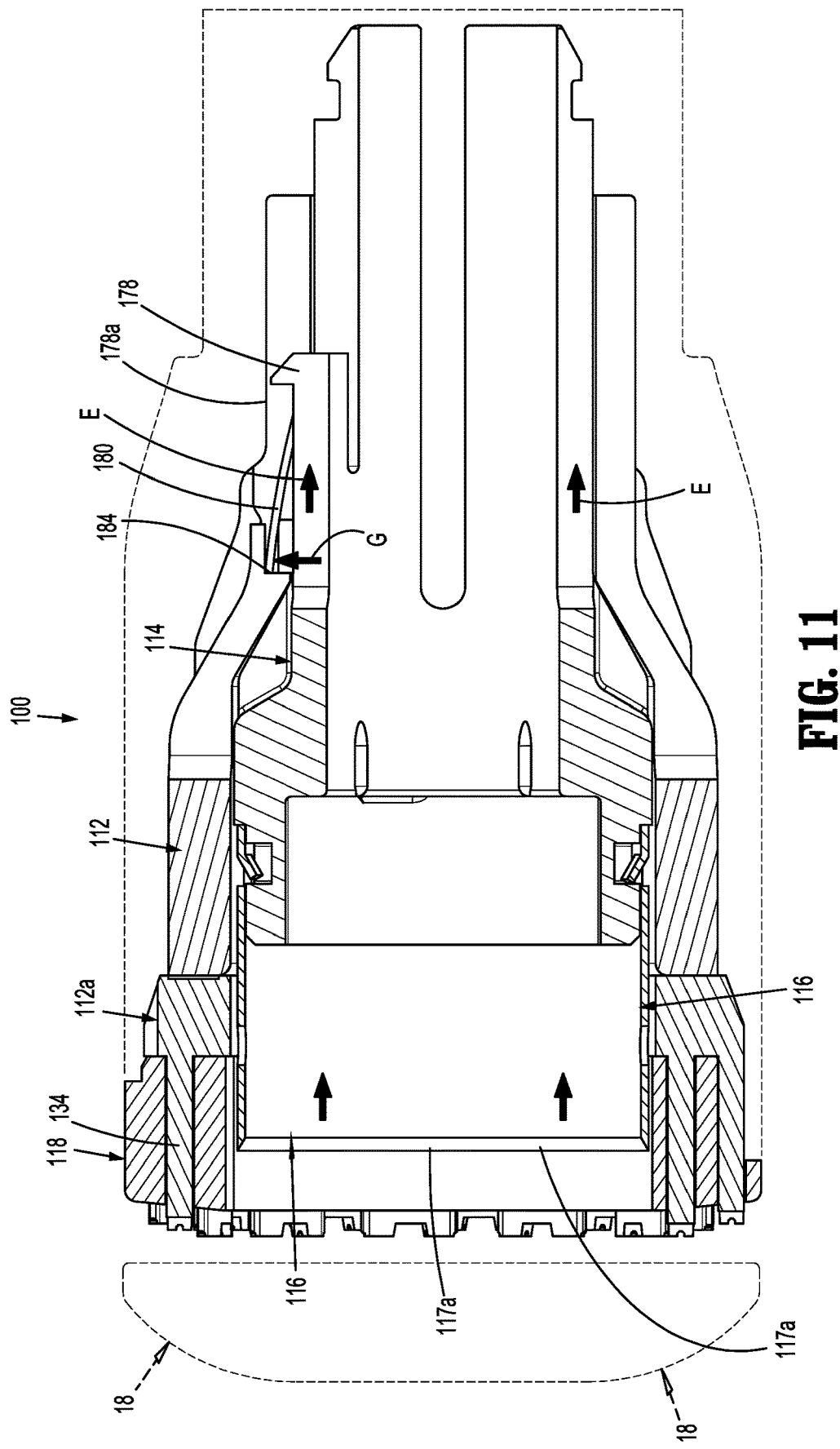
FIG. 11 is a cross-sectional view taken along section line 8-8 of FIG. 2 with the reload assembly in a fired state and the knife carrier in its retracted locked out position.

FIGS. 10 and 11 illustrate the reload assembly 100 as the knife carrier 114 is moved from its advanced position to its retracted position after the reload assembly is fired. When the knife carrier 114 is moved proximally in the direction indicated by arrows "E" towards its retracted position, the annular knife 116 is also moved proximally to a position located within the shell housing 110. In this position, a clinician is protected from inadvertent injury caused by the cutting edge 117a of the annular knife 116. As the knife carrier 114 and annular knife 116 are moved proximally within the shell housing 110, the staple actuator 112 remains in an advanced position within the shell housing 110. As the knife carrier 114 moves proximally in relation to the staple actuator 112, each of the locking members 180 engages a portion of the staple actuator 112 that defines a respective stop surface 184 such that the locking members 180 are deformed inwardly towards the outer surface of the knife carrier 114 in the direction indicated by arrow "F" in FIG. 10. In their deformed state, the locking members 180 pass inwardly and move proximally beyond the respective stop surfaces 184 (FIG. 11). When the locking members 180 move proximally past the respective stop surfaces 184, the locking members 180 spring outwardly to their undeformed state in the direction indicated by arrow "G" in FIG. 11 to positions aligned with the respective stop surfaces 184. In this position, the locking members 180 prevent readvancement of the knife carrier 112 to retain the annular knife 116 within the shell housing 110 of the reload assembly 100.

Figure 12:
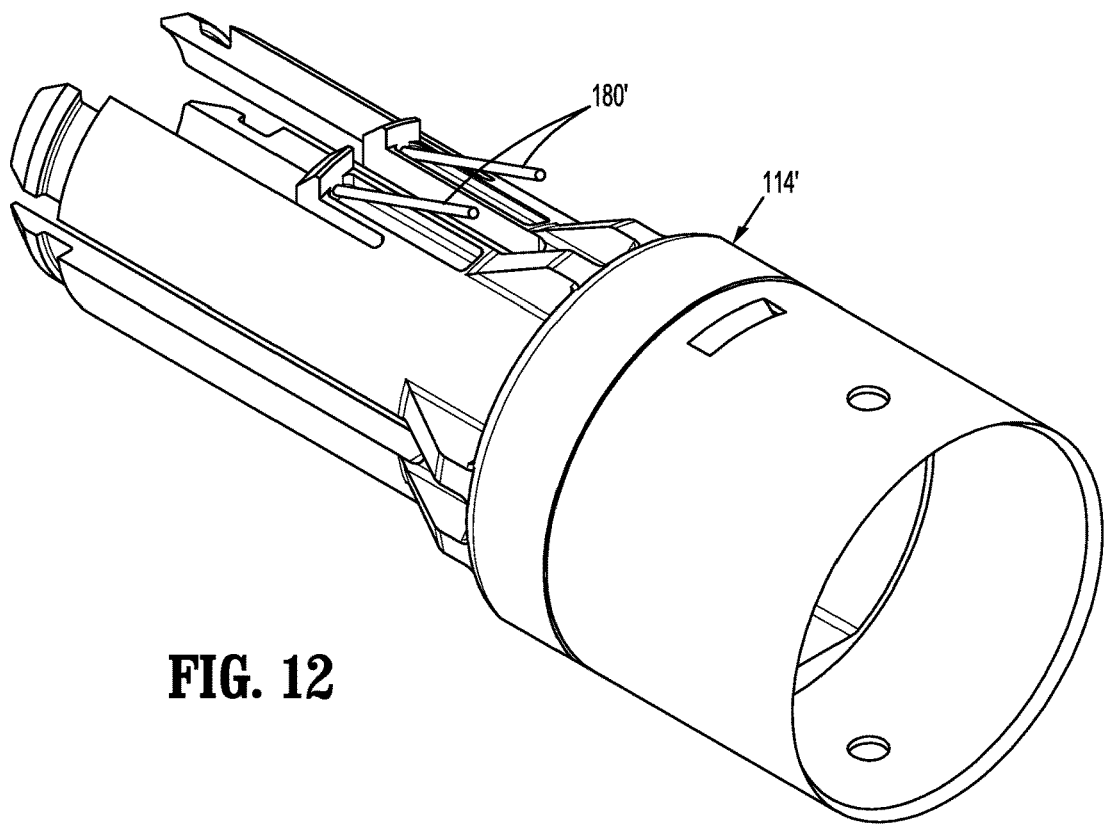
FIG. 12 is a side perspective view from the distal end of an alternate embodiment of the knife carrier of the reload assembly shown in FIG. 2.
Figure 13:
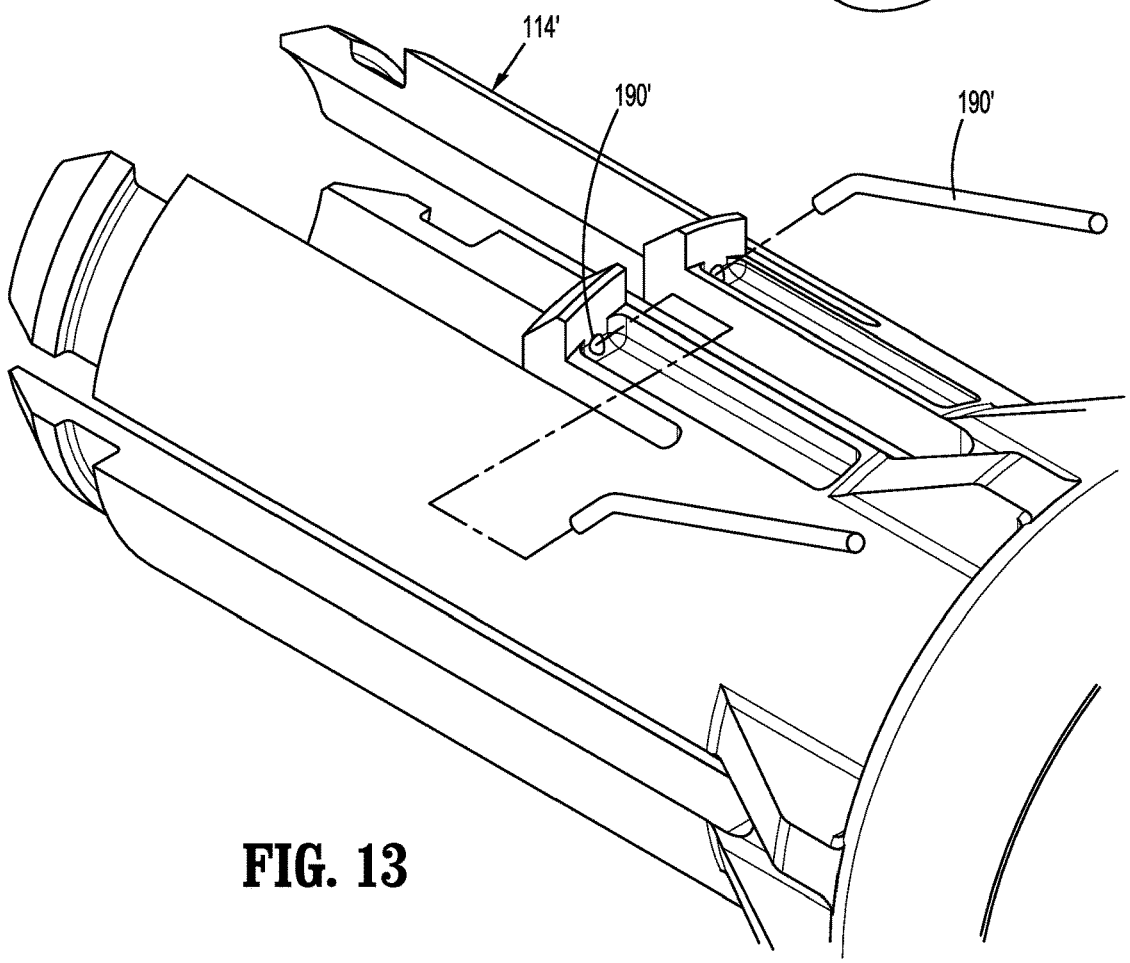
FIG. 13 is a side perspective view of a proximal portion of the knife carrier shown in FIG. 12 with lockout members removed from a body of the knife carrier.

The locking members 180 may be provided in a variety of different configurations and formed of a variety of different materials. In addition, the locking members 180 may be formed integrally with the knife carrier 114 or formed separately from the knife carrier 114 and secured to the knife carrier 114 using any known fastening technique. For example as illustrated in FIGS. 3-11, the locking member 180 may be in the form of a flat or rectangular leaf spring that is formed from a deformable resilient material such as spring steel or plastic and received within a recess 190 formed in the knife carrier 114 in cantilevered fashion. Alternately, other materials and configurations may be used to form the locking member 180. In one alternate embodiment shown in FIGS. 12 and 13, each of the locking members 180' is formed from a resilient wire. In embodiments, the resilient wire 180' has a circular cross-sectional shape and is received within a recess 190' formed in the knife carrier 114 in cantilevered fashion. Alternately other cross-sectional shapes are envisioned.

Figure 14:
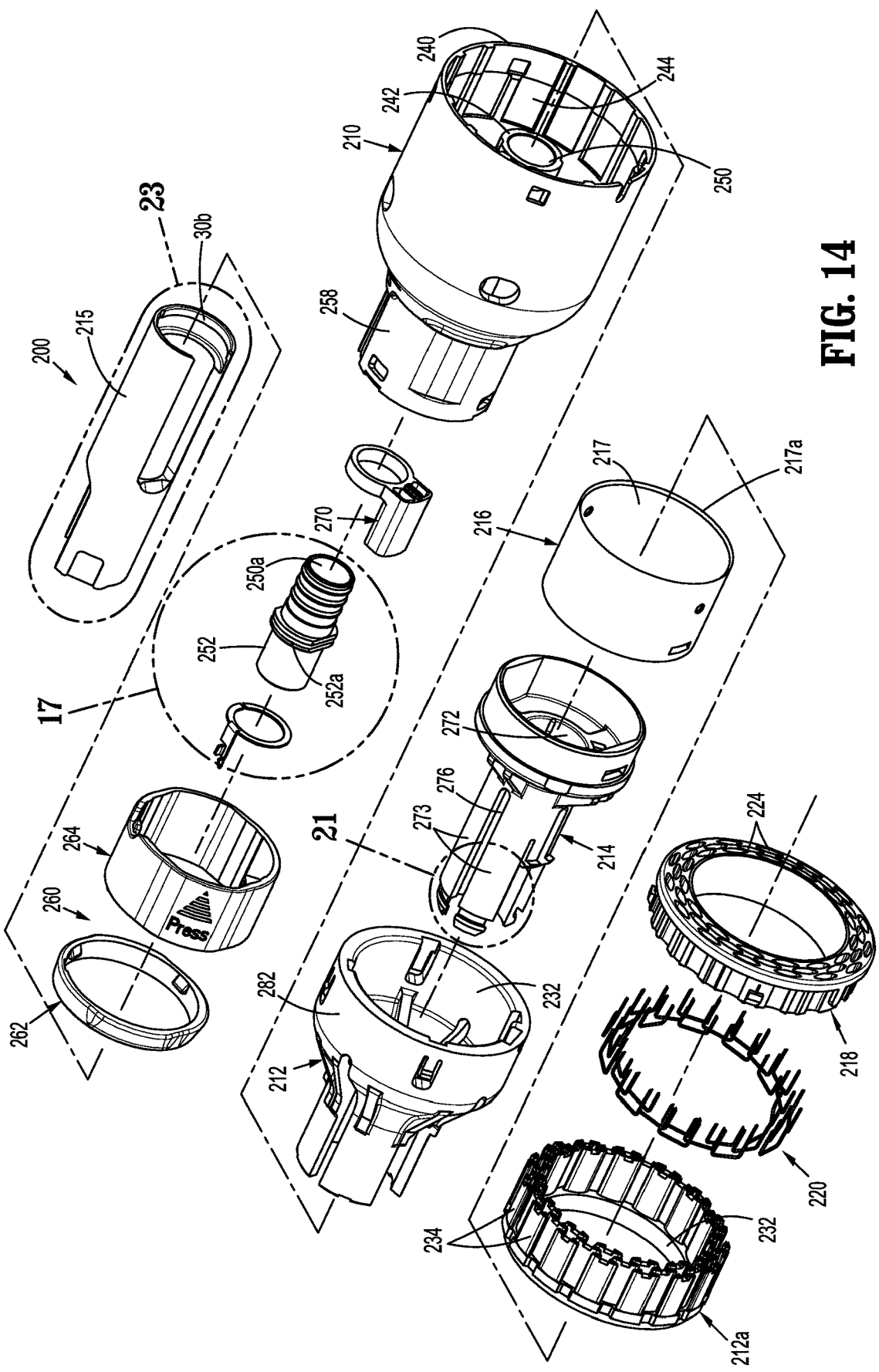
FIG. 14 is side perspective exploded view from the distal end of another exemplary embodiment of a reload assembly of the stapling device shown in FIG. 1.
Figure 15:
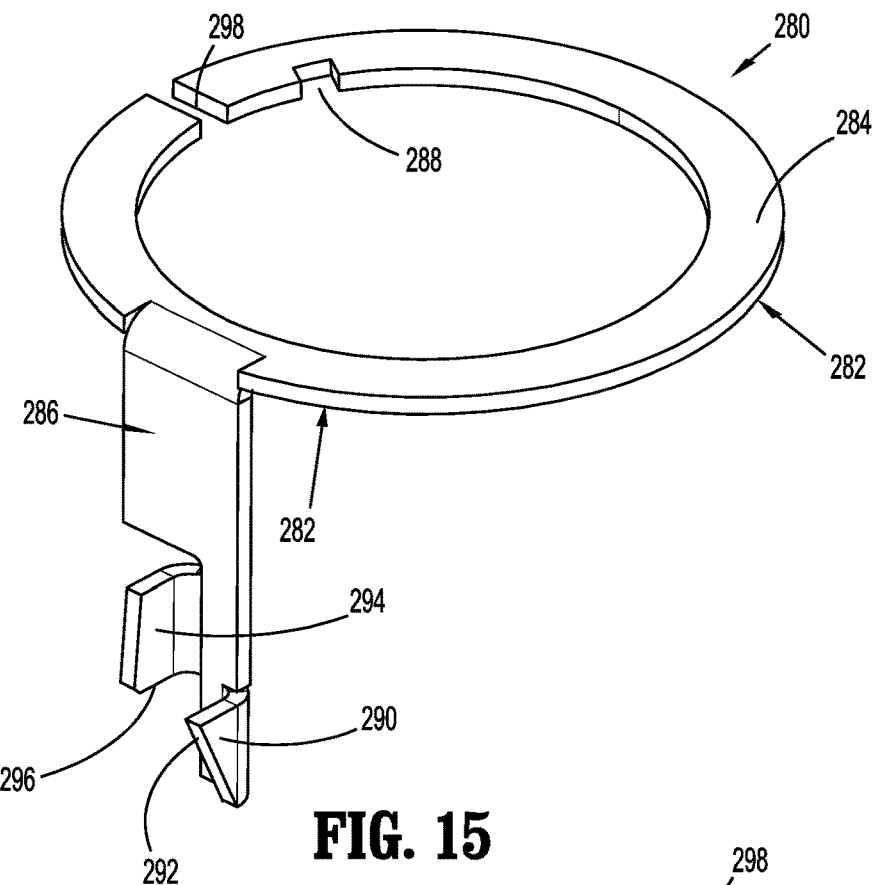
FIG. 15 is a side perspective view from the proximal end of a lockout member of the reload assembly shown in FIG. 14.
Figure 16:
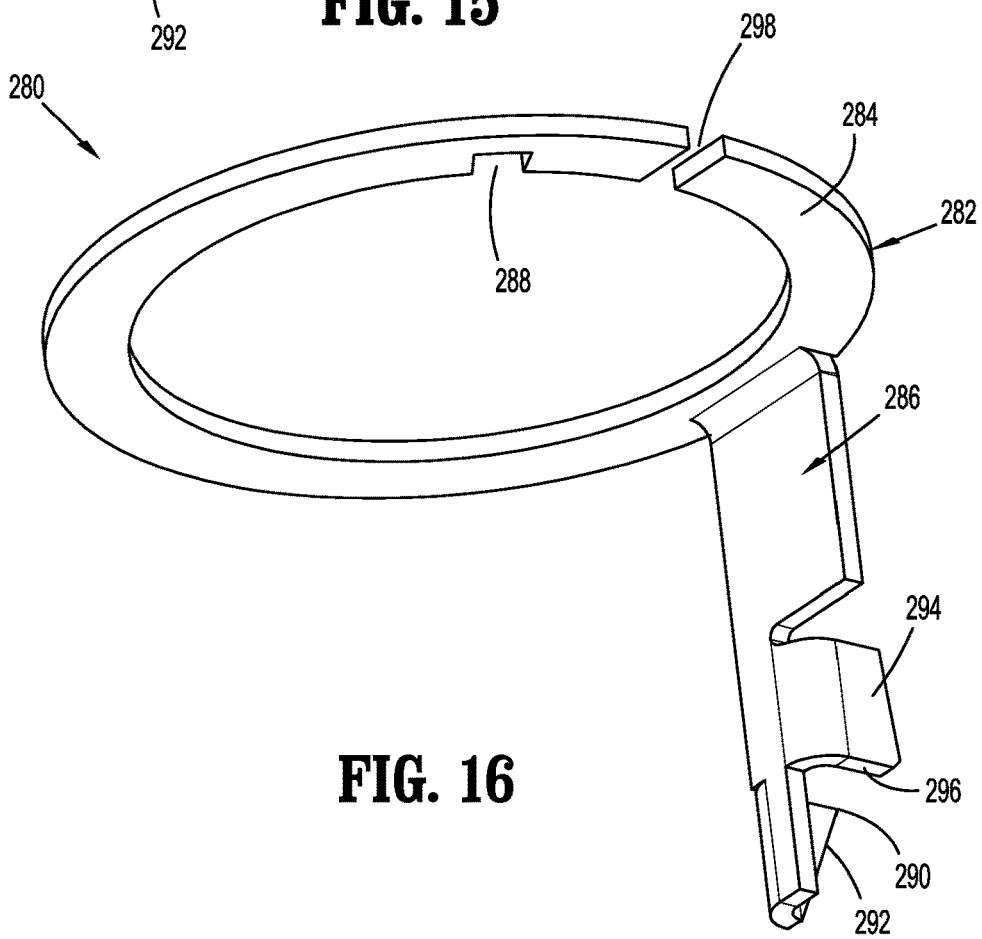
FIG. 16 is a side perspective view from the distal end of the lockout member of the reload assembly shown in FIG. 14.
Figure 17:
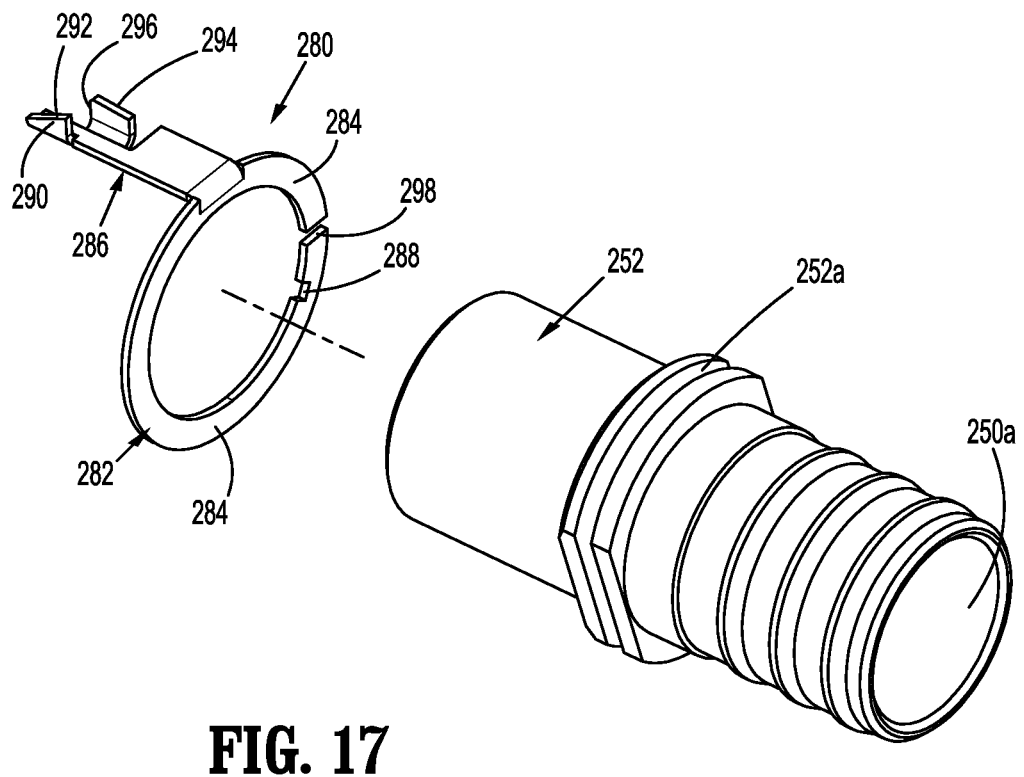
FIG. 17 is an enlarged view of the indicated area of detail shown in FIG. 14.
Figure 18:
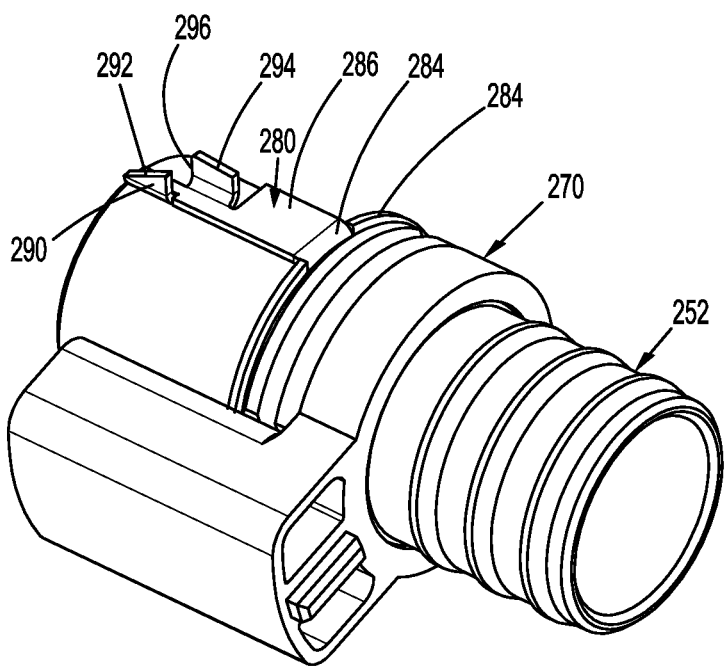
FIG. 18 is a side perspective view from the distal end of the lockout member shown in FIG. 15 secured to a bushing of a shell housing of the reload assembly shown in FIG. 14.
Figure 19:
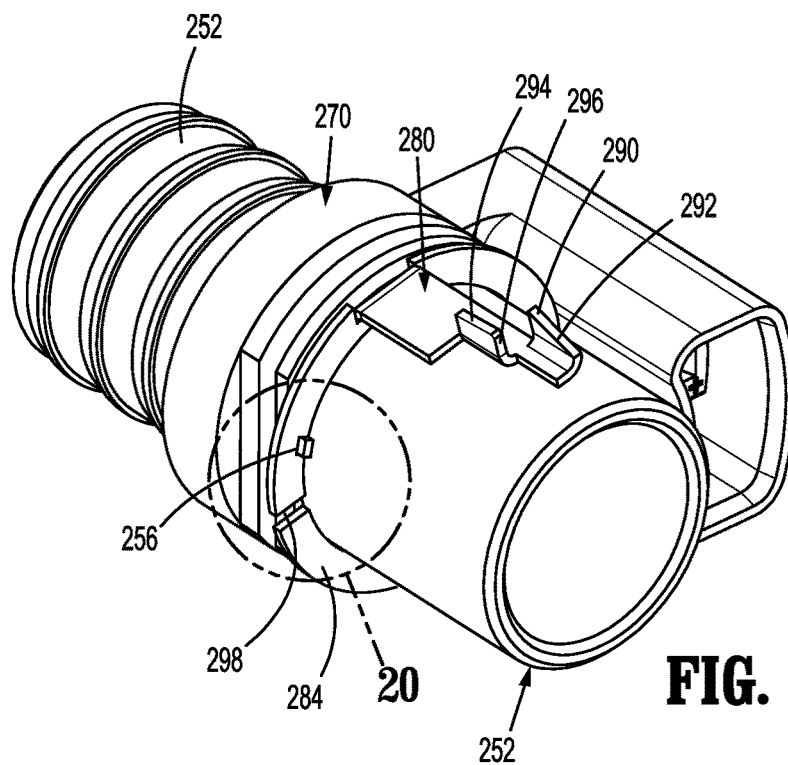
FIG. 19 is a side perspective view from the proximal end of the lockout member shown in FIG. 15 secured to the bushing of the shell housing of the reload assembly shown in FIG. 14.

FIGS. 14-33A illustrate another exemplary embodiment of the disclosed reload assembly shown generally as reload assembly 200. FIG. 14 illustrates the reload assembly 200 which can be used with the stapling device 10 (FIG. 1) and includes a shell housing 210, a staple actuator 212, a staple pushing member 212a, a knife carrier 214, an annular knife 216 supported on the knife carrier 214, a staple cartridge 218, and a plurality of staples 220 supported within the staple cartridge 218. The adaptor assembly 14 (FIG. 1) includes a knife carrier driver 215 that interacts with the knife carrier 214 to move the knife carrier 214 within the shell housing 210. The staple cartridge 218 is annular and defines annular rows of staple pockets 224. Each of the staple pockets 224 supports one staple of the plurality of staples 220. The staple actuator 212 and the staple pushing member 212a together define a longitudinal through bore 232 (FIG. 26). The staple actuator 212 has a distal portion that abuts a proximal portion of the staple pushing member 212a such that distal movement of the staple actuator 212 within the shell housing 210 causes distal movement of the staple pushing member 212a within the shell housing 210. The staple pushing member 212a of the reload assembly 200 has a plurality of fingers 234. Each of the plurality of fingers 234 is received within a respective one of the staple pockets 224 of the staple cartridge 218 and is movable through the respective staple pocket 224 to eject a staple 220 from the respective staple pocket 224 when the staple pushing member 212a is moved from a retracted position to an advanced position within the shell housing 210.

The shell housing 210 includes an outer housing portion 240 and an inner housing portion 242 that are spaced from each other to define an annular cavity 244 between the outer and inner housing portions 240 and 242. The staple actuator 212 and the staple pushing member 212a are movable within the annular cavity 244 of the shell housing 210 from a retracted position to an advanced position to eject the staples 220 from the staple cartridge 218.

The annular knife 216 is supported about an outer surface of the knife carrier 214, defines a cylindrical cavity 217, and includes a distal cutting edge 217a. The knife carrier 214 and annular knife 216 are positioned within the through bore 232 of the staple actuator 212 and movable from retracted positions to advanced positions to cut tissue positioned radially inward of the staple cartridge 218.

The inner housing portion 242 of the shell housing 210 defines a through bore 250 that receives an anvil shaft (not shown) of the anvil assembly 18 (FIG. 1). For a more detailed description of an exemplary anvil assembly 18, see, e.g., the '106 Patent. The through bore 250 has a proximal portion that receives a bushing 252 that defines a through bore 250a that is coaxial and forms an extension of the through bore 250 of the inner housing portion 242. In embodiments, the bushing 252 is formed of a high strength material, e.g., metal, to provide added strength to the inner housing portion 242 of the shell housing 210 and includes an annular flange 252a. The annular flange 252 includes a protrusion 253.

The shell housing 210 includes a proximal portion 258 that supports a coupling mechanism 260 that is operable to releasably couple the reload assembly 200 to the adaptor assembly 14 of the stapling device 10 (FIG. 1). The coupling mechanism 260 allows for removal and replacement of the reload assembly 200 to facilitate reuse of the stapling device 10. The coupling mechanism 260 includes a retaining member 262 and a coupling member 264. The coupling member 264 is received about the proximal portion 258 of the shell housing 210 and is configured to engage the distal portion 14a (FIG. 1) of the adaptor assembly 14 to couple the reload assembly 200 to the adaptor assembly 14. It is envisioned that other coupling mechanisms can be used to secure the reload assembly 200 to the adaptor assembly 14. Alternately, the reload assembly 200 can be non-removably secured to the adaptor assembly 14.

The reload assembly 200 may include an e-prom holder 270 that is supported on the shell housing 210 and is configured to support an e-prom (not shown). As is known in the art, an e-prom communicates with the adaptor assembly 14 (FIG. 1) to provide information to the adaptor assembly 14 and the handle assembly 12 (FIG. 1) regarding characteristics of the reload assembly 10. In some embodiments, the e-prom holder 270 can be received about a distal portion of the bushing 52.

The knife carrier 214 includes a plurality of resilient longitudinal body portions 273 that are spaced from each other and together define a central bore 272. The central bore 272 of the knife carrier 214 receives the inner housing portion 242 of the shell housing 210 such that the knife carrier 214 is movable about the inner housing portion 242 of the shell housing 210 between a retracted position and an advanced position. The longitudinal body portions 273 of the knife carrier 214 are resilient and spaced from each other to define slots 276 that receive guide portions (not shown) of the shell housing 210 to limit the knife carrier 214 to longitudinal movement within the shell housing 210.

The staple actuator 212 includes a body that is also received about the inner housing portion 242 of the shell housing 210 and is movable within the shell housing 210 from a retracted position to an advanced position. The body defines a plurality of guide slots 281 that receive the guide members (not shown) of the shell housing 210 to limit the staple actuator 212 to longitudinal movement within the shell housing 210.

Figure 20:
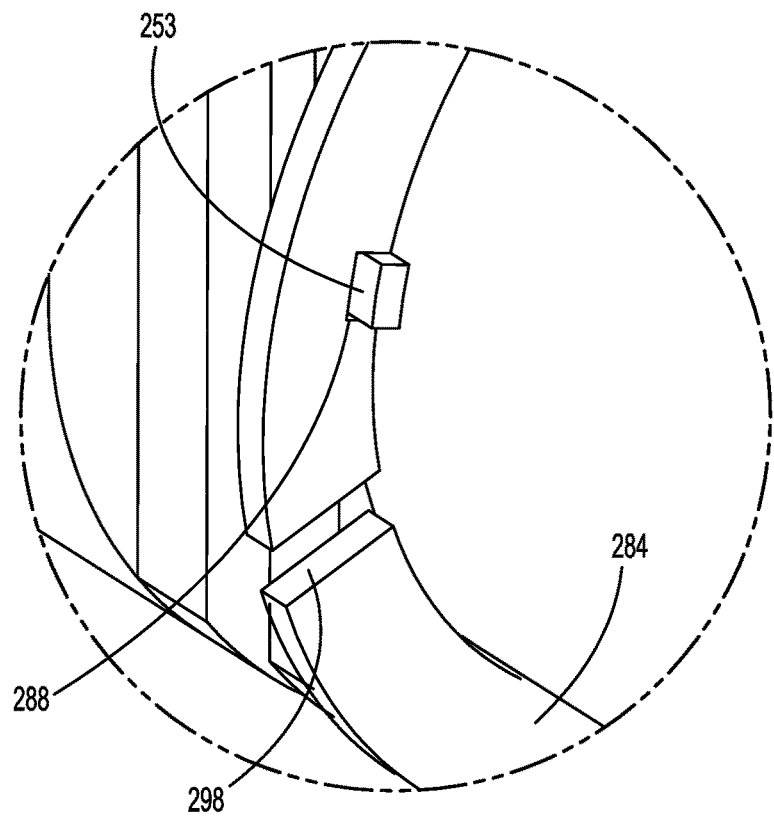
FIG. 20 is an enlarged view of the indicated area of detail shown in FIG. 19.

FIGS. 14-20 illustrate a locking member 280 of the reload assembly 200 that includes a body 282 having an annular ring 284 and a lockout latch 286. The annular ring 284 is received about a proximal portion of the bushing 252 and is positioned in abutting relation to the flange 252a to secure the locking member 280 to the bushing 252 (FIG. 14). The annular ring 284 defines a cutout 288 which may be rectangular in shape and receives the protrusion 253 formed on the bushing 252 to prevent rotation of the locking member 280 in relation to the bushing 252 (FIG. 20). In embodiments, the annular ring 280 of the locking member 280 may include a slot 298 to allow for radial flexing of the annular ring 280 to facilitate placement of the locking member 280 in a friction fit manner about the bushing 252.

The lockout latch 286 is formed of a resilient material and extends in cantilevered fashion from the annular ring 284. In embodiments, the lockout latch 286 is integrally formed with the annular ring 280 of the locking member. Alternately, the lockout latch 286 can be pivotably secured to the annular ring 280 in cantilevered fashion using, e.g., a hinge mechanism (not shown). The lockout latch 286 includes a first tab 290 that has an angled proximally facing surface 292 and a second tab 294 that has a substantially perpendicular proximally facing surface 296. In embodiments, the first tab 290 has a generally triangular shape and the second tab 294 has a generally rectangular shape. Alternately, other configurations are envisioned. The lockout latch 286 is movable from an unbiased position in which the lockout latch 286 is spaced outwardly of and extends along an outer surface of the bushing 252 to a biased position in which the lockout latch 286 is biased inwardly towards the outer surface of the bushing 252.

Figure 21:
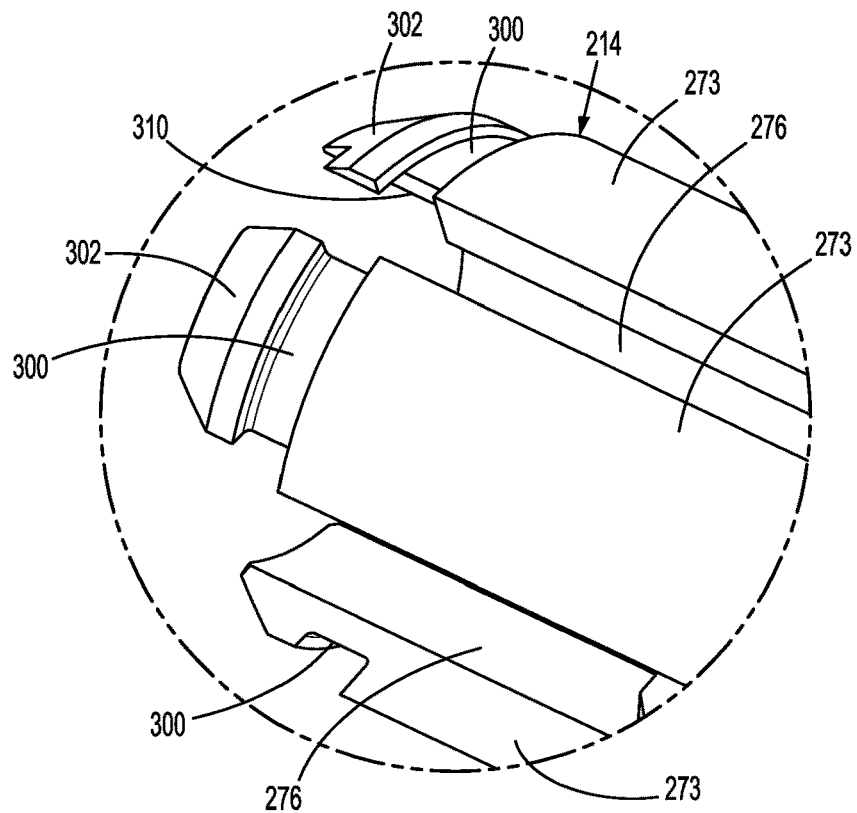
FIG. 21 is an enlarged view of the indicated area of detail shown in FIG. 14.
Figure 22:
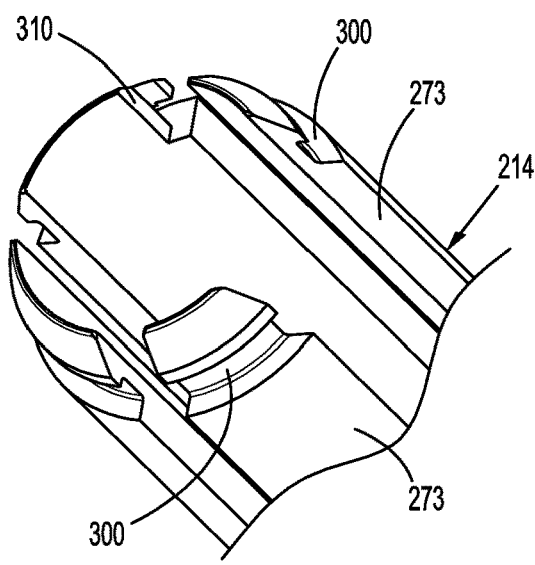
FIG. 22 is an enlarged view of a proximal portion of a knife carrier of the reload assembly shown in FIG. 14.
Figure 25:
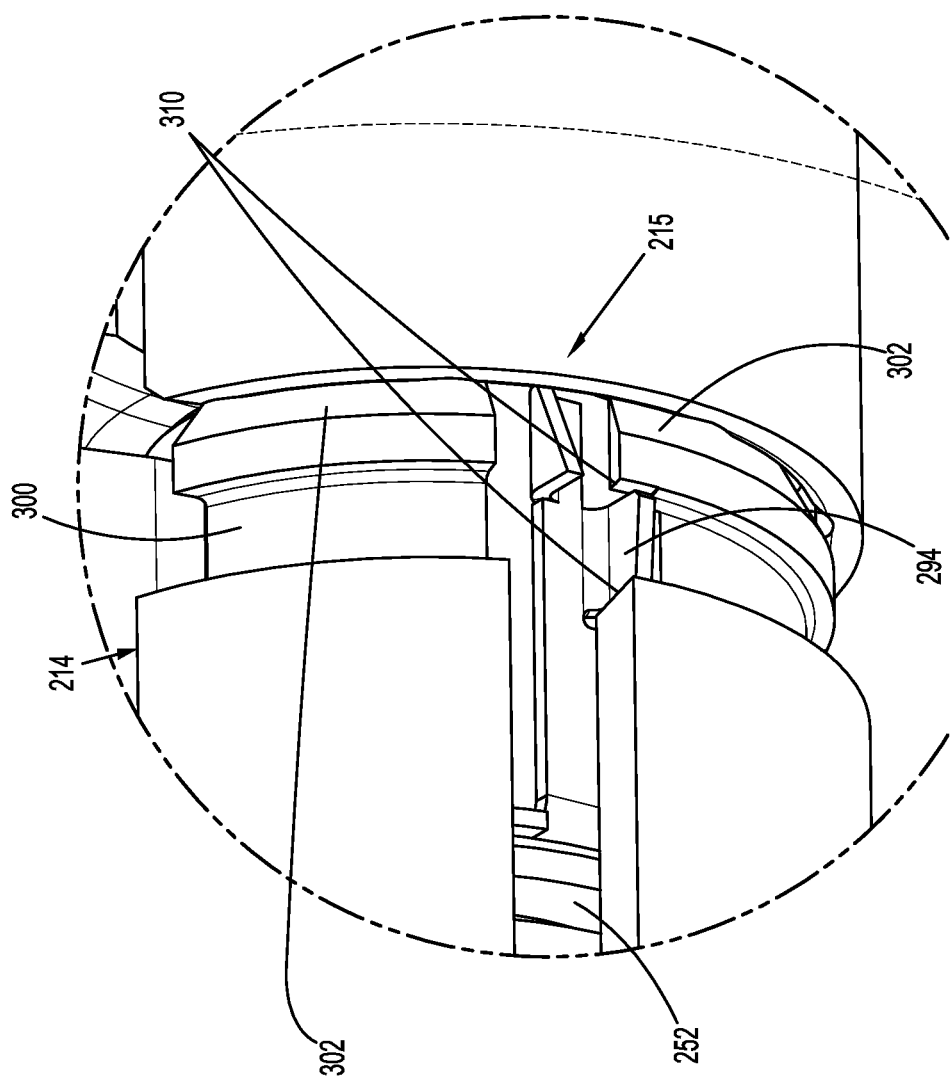
FIG. 25 is an enlarged view of the indicated area of detail shown in FIG. 23.
Figure 28:
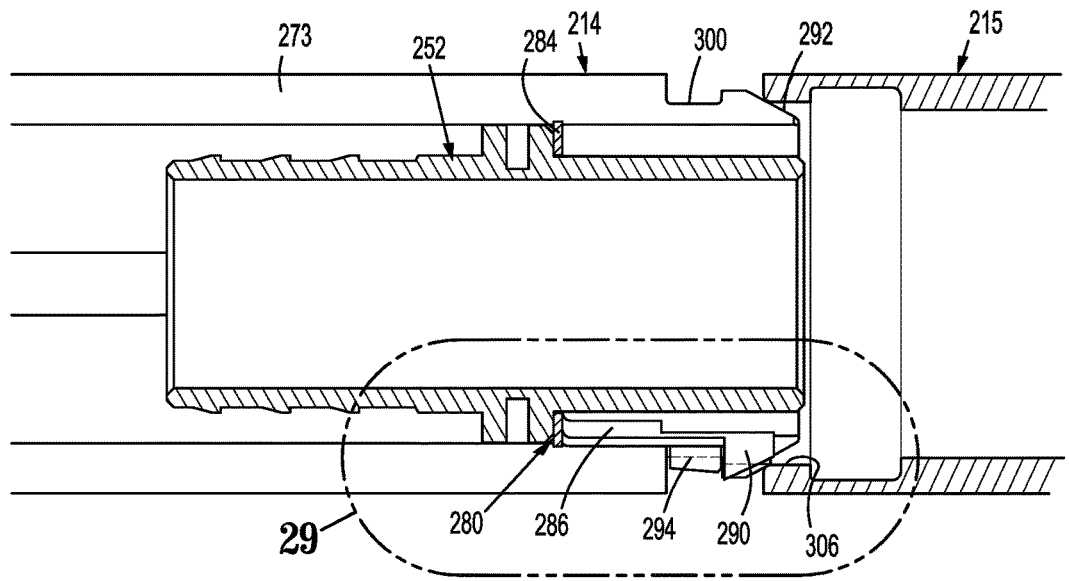
FIG. 28 is a side cross-sectional view taken through the bushing and the knife carrier of the reload assembly shown in FIG. 14 and through a knife carrier driver of the stapling device shown in FIG. 1 with the knife carrier driver and knife carrier in retracted positions.
Figure 29:
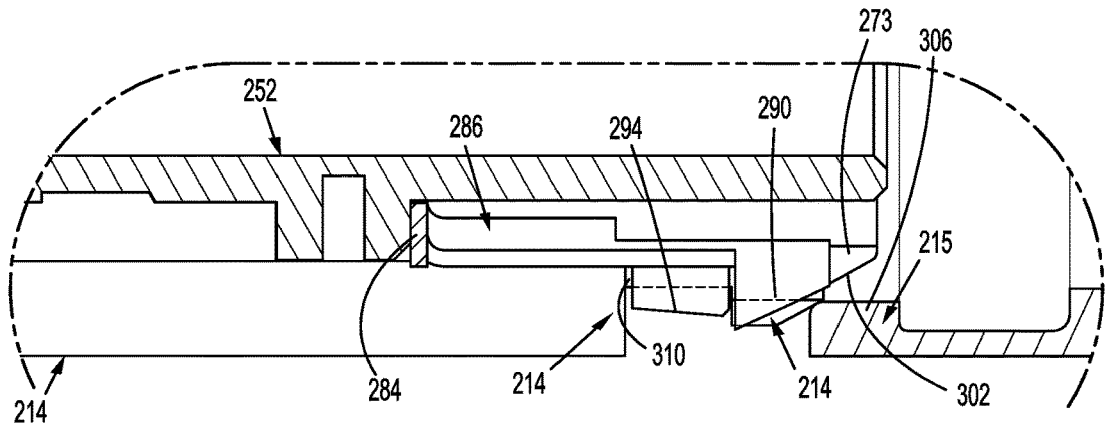
FIG. 29 is an enlarged view of the indicated area of detail shown in FIG. 28 with the knife carrier driver and knife carrier in retracted positions and the lockout member in a latched position.
Figure 30:
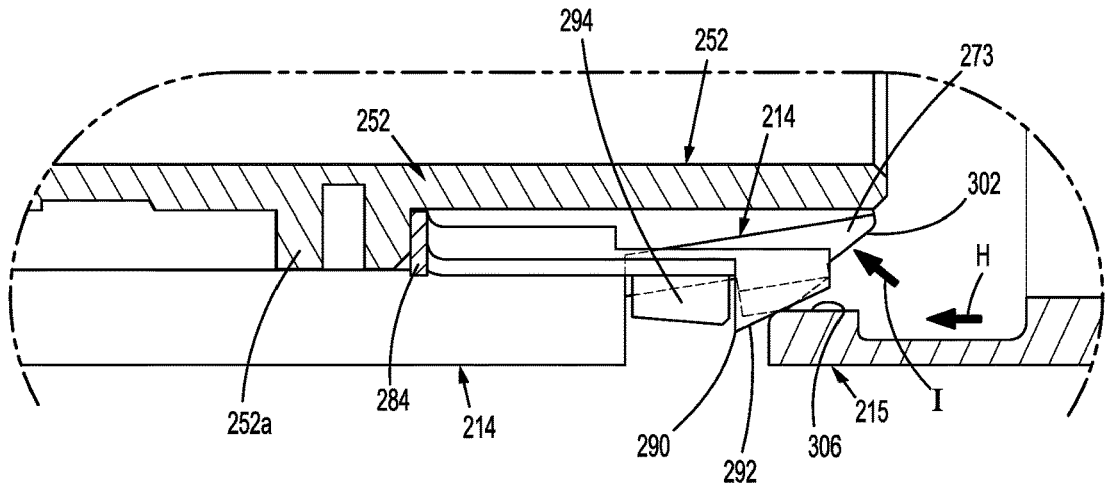
FIG. 30 is an enlarged view of the indicated area of detail shown in FIG. 28 with the knife carrier driver partially advanced into engagement with the knife carrier and the locking member and the locking member being biased towards an unlatched position.

FIGS. 21-23 illustrate a proximal portion of the longitudinal body portions 273 of the knife carrier 214. Each of the longitudinal body portions 273 of the knife carrier 214 defines an annular recess 300 and a tapered surface 302 that is positioned proximally of the annular recess 300. The knife carrier driver 215 (FIG. 23) of the adaptor assembly 14 includes an inner annular rib 306 that is received within the annular recesses 300 of the longitudinal body portions 273 to couple the knife carrier driver 215 to the knife carrier 214 when the stapling device 10 (FIG. 1) is actuated to fire staples 220 (FIG. 14) from the reload assembly 200. One of the longitudinal body portions 273 also defines a notch 310 that receives the second tab 294 of the locking member 280 when the knife carrier 214 is in a retracted position within the shell housing 210 to obstruct distal movement of the knife carrier within the shell housing 210.

FIGS. 24-29 illustrate the reload assembly 200 in a pre-fired state with the knife carrier 214, the knife driver 215, the staple actuator 212, and the staple pushing member 212a in their retracted positions. In the pre-fired state, the distal end of the knife driver 215 is positioned adjacent to a proximal end of the knife carrier 214 and adjacent to the lockout latch 286 of the locking member 280. In this position, the inner annular rib 306 at the distal end portion of the knife driver 215 is spaced proximally of the annular recesses 300 formed in the longitudinal body portions 273 of the knife carrier 214. In addition, the lockout latch 286 is in its undeformed state with the first tab 290 of the lockout latch 286 located adjacent to the distal end of the knife driver 215 and the second tab 294 received within the notch 310 formed in the longitudinal body portion 273 of the knife carrier 214. When the second tab 294 positioned within the notch 310, the proximally facing surface 296 of the second tab 294 obstructs advancement of the knife carrier 214 within the shell housing 210.

FIGS. 30-33 illustrate the reload assembly 200 as the knife driver 215 is moved towards its advanced position to move the knife carrier 214 and the annular knife 216 toward their advanced positions. When the knife driver 215 is advanced within the shell housing 210 in the direction indicated by arrow "H" in FIG. 30, the distal end portion of the knife driver 215 engages the tapered surface 302 at the proximal end portion of each of the longitudinal body portions 273 of the knife carrier 214 to urge the longitudinal body portions 273 inwardly in the direction indicated by arrow "I" in FIG. 30. This allows the inner annular rib 306 of the knife driver 215 to pass into the annular recesses 300 of the longitudinal body portions 273 of the knife carrier 214 to couple the distal end portion of the knife driver 215 to the proximal end portion of the knife carrier 214.

Figure 31:
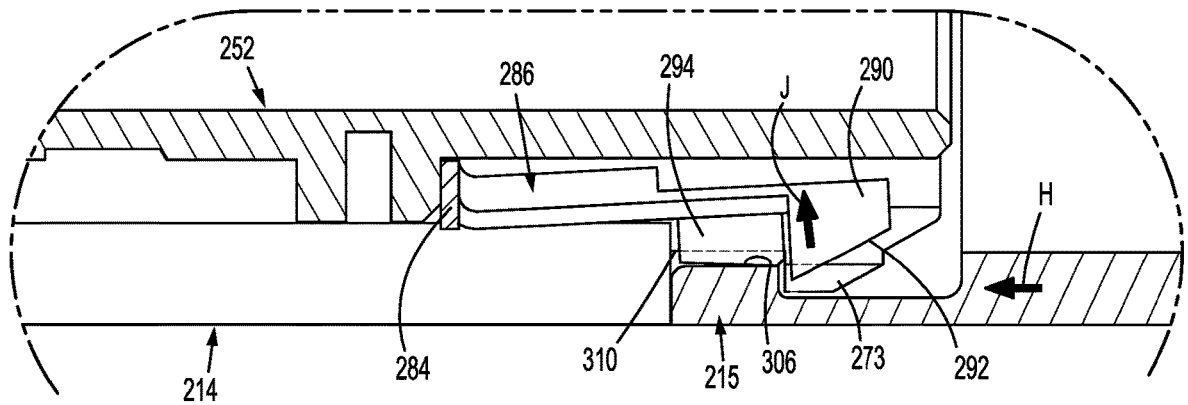
FIG. 31 is an enlarged view of the indicated area of detail shown in FIG. 28 with the knife carrier driver advanced into engagement with the knife carrier and the locking member biased to the unlatched position.
Figure 32:
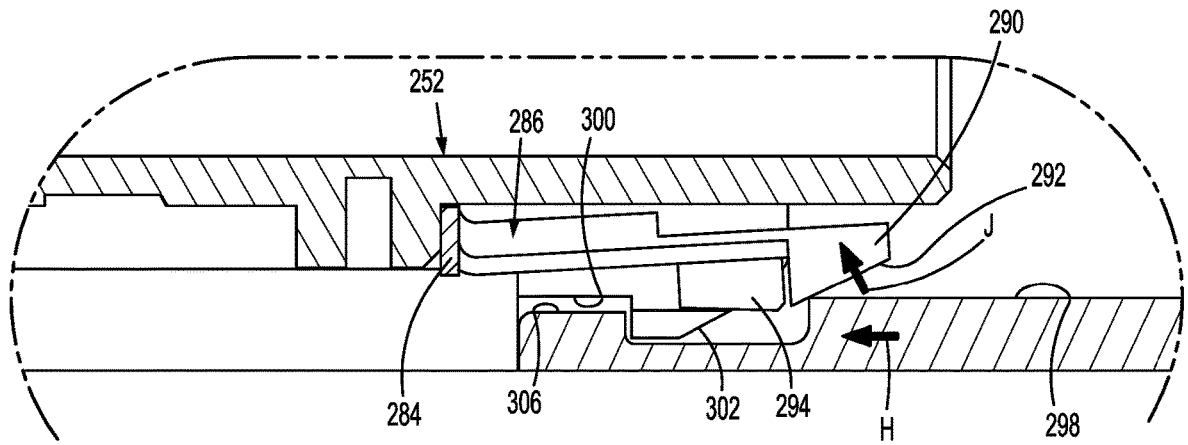
FIG. 32 is an enlarged view of the indicated area of detail shown in FIG. 28 with the knife carrier driver coupled to the knife carrier and the locking member biased to the unlatched position as the knife carrier driver and knife carrier move together towards an advanced position.

As the knife driver 215 continues to advance within the shell housing 210 in the direction indicated by arrow "H" in FIG. 31, the distal end portion of the knife driver 215 also engages the angled proximally facing surface 292 of the first tab 290 to urge the lockout latch 286 inwardly in the direction indicated by arrow "J" towards its deformed state. As the lockout latch 286 moves inwardly towards the bushing 252 to its deformed state, the second tab 294 of the lockout latch 286 is removed from the notch 310 formed in the proximal end of the respective longitudinal body portion 273 of the knife carrier 214. In this position, the second tab 294 does not obstruct advancement of the knife carrier 214 within the shell housing 210. As the knife driver 215 advances within the shell housing 210, engagement between the knife driver 215 and the first tab 290 retains the lockout latch 286 in its deformed state with the second tab 294 removed from the notch 310 to allow the knife carrier 214 and the knife driver 215 to move to their advanced positions to advance the annular knife 216 to its advanced position extending from the shell housing 210 to cut tissue.

Figure 33:
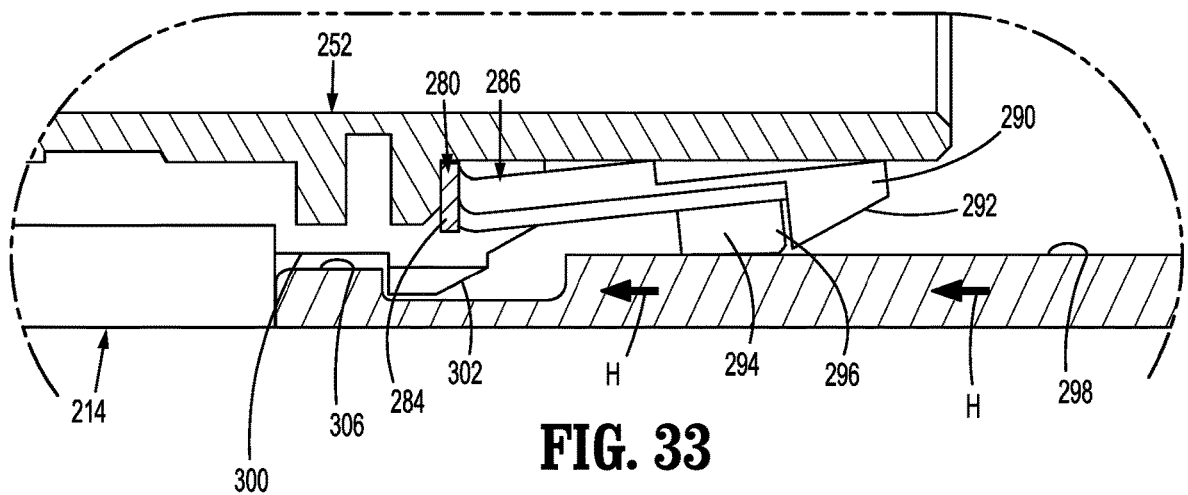
FIG. 33 is an enlarged view of the indicated area of detail shown in FIG. 28 with the knife carrier driver coupled to the knife carrier and the locking member retained in the unlatched position as the knife carrier driver and knife carrier move together towards the advanced position to cut tissue.
Figure 33A:
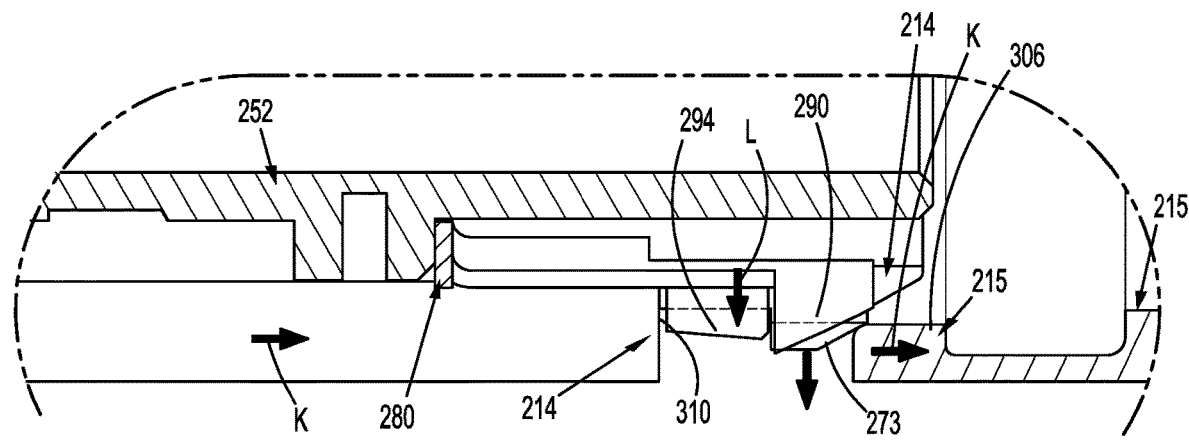
FIG. 33A is an enlarged view of the indicated area of detail shown in FIG. 28 with the knife carrier driver returned to its retracted position after firing uncoupled from the knife carrier and the locking member returned to the latched position.

FIG. 33A illustrates the reload assembly 200 as the knife carrier 214 and the knife driver 215 are moved from their advanced positions back to their retracted positions in the direction indicated by arrows "K". This movement retracts the annular knife 216 into the shell housing 210. When the knife carrier 214 reaches its retracted position and cannot move further proximally, the longitudinal body portions 273 are forced inwardly by the inner annular rib 306 of the knife driver 215 such that the inner annular rib 306 is removed from the annular recesses 300 of the longitudinal body portions 273 of the knife carrier 214 to uncouple the knife driver 215 from the knife carrier 214. When the notch 310 in the longitudinal body portion 273 of the knife carrier 214 becomes aligned with the second tab 294 of the lockout latch 286 of the locking member 280, the lockout latch 286 pivots in the direction indicated by arrow "L" in FIG. 33A to reposition the second tab 294 within the notch 310. Once again, this obstructs advancement of the knife carrier 214 to prevent readvancement of the annular knife 216 from within the shell housing 210.

Figure 34:
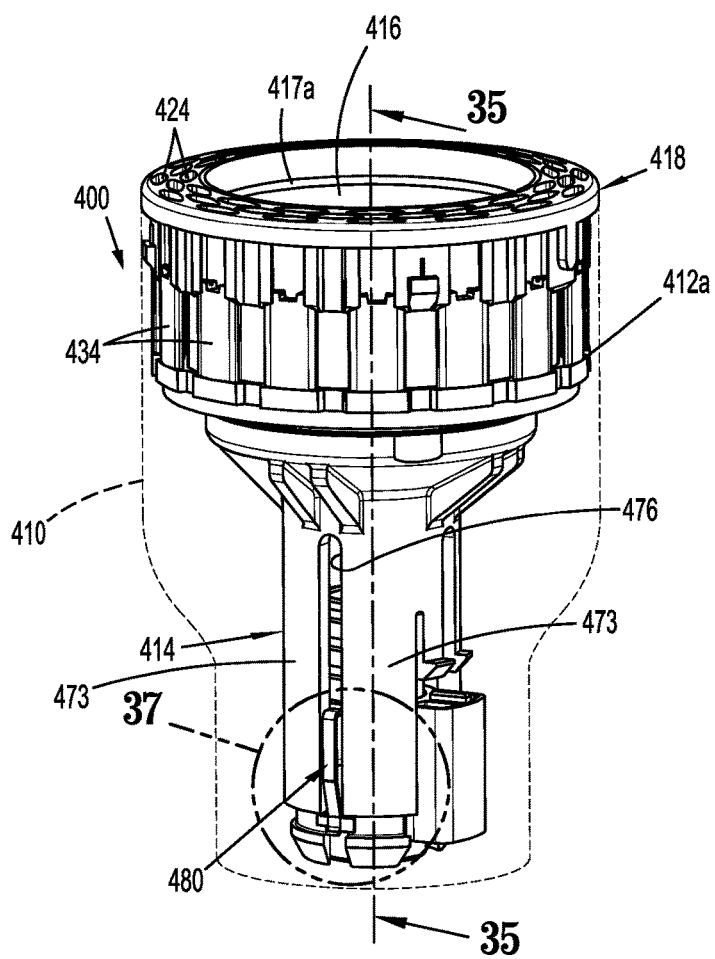
FIG. 34 is side perspective view of another exemplary embodiment of a reload assembly of the stapling device shown in FIG. 1.
Figure 35:
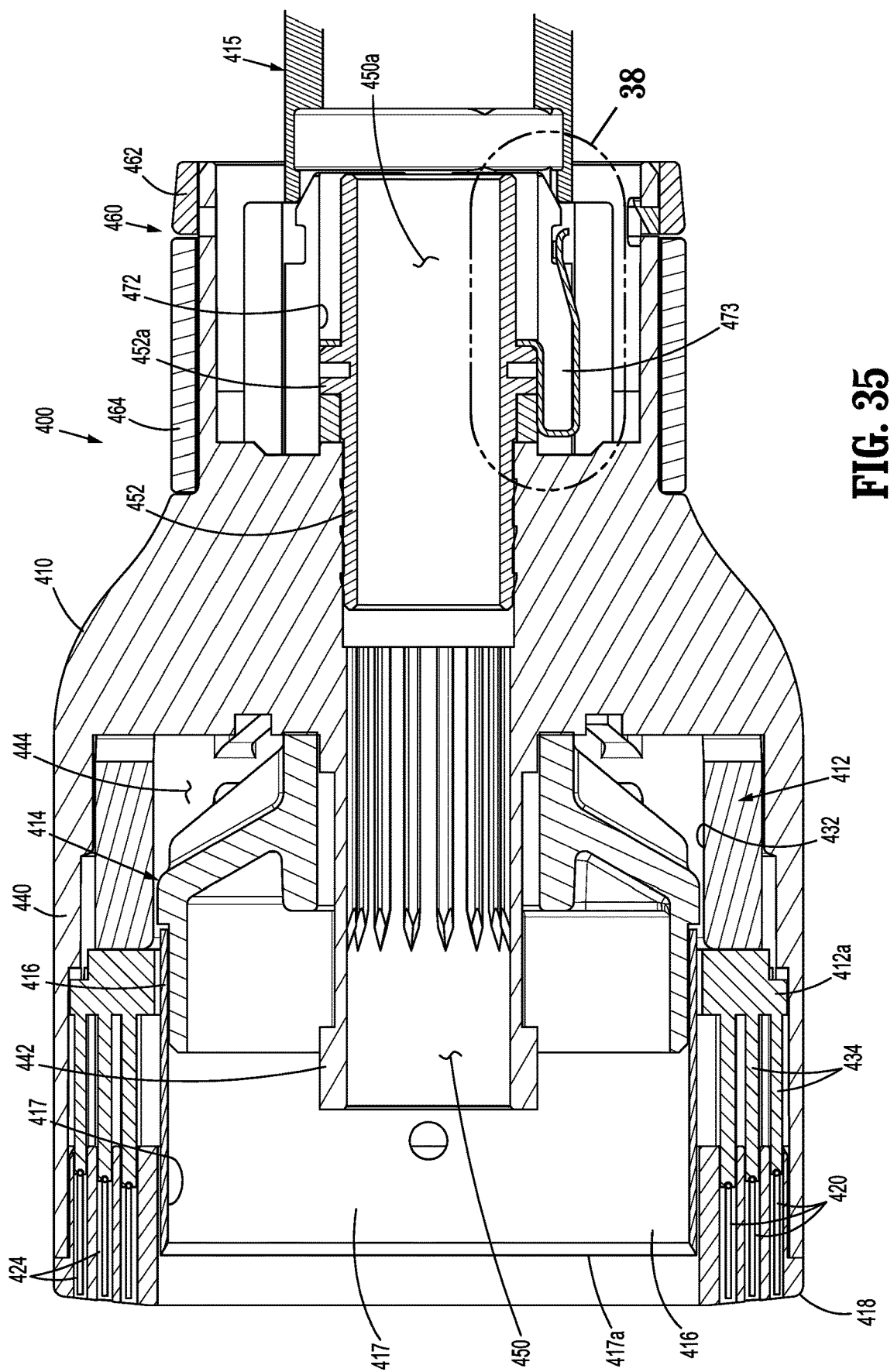
FIG. 35 is a cross-sectional view taken along section line 35-35 of FIG. 34 with the reload assembly in a pre-fired state.

FIGS. 34-42 illustrate another exemplary embodiment of the disclosed reload assembly shown generally as reload assembly 400 which can be used with the stapling device 10 (FIG. 1). FIGS. 34 and 35 illustrate another exemplary embodiment of the reload assembly shown generally as reload assembly 400. Reload assembly 400 includes a shell housing 410, a staple actuator 412, a staple pushing member 412a, a knife carrier 414, an annular knife 416 supported on the knife carrier 414, a staple cartridge 418, and a plurality of staples 420 supported within the staple cartridge 418. The adaptor assembly 14 (FIG. 1) includes a knife carrier driver 415 (FIG. 35) that interacts with the knife carrier 414 to move the knife carrier 414 from a retracted position to an advanced position within the shell housing 410 as described in detail below. The staple cartridge 418 is annular and defines annular rows of staple pockets 424. Each of the staple pockets 424 supports one of the plurality of staples 420. The staple actuator 412 and the staple pushing member 412a together define a longitudinal through bore 432 (FIG. 35). The staple actuator 412 has a distal portion that abuts a proximal portion of the staple pushing member 412a such that distal movement of the staple actuator 412 within the shell housing 410 causes distal movement of the staple pushing member 412a within the shell housing 410. The staple pushing member 412a of the reload assembly 400 has a plurality of fingers 434. Each of the plurality of fingers 434 is received within a respective one of the staple pockets 424 of the staple cartridge 418 and is movable through the respective staple pocket 424 to eject a staple 420 from a respective pocket 424 of the staple cartridge 418 when the staple pushing member 412a is moved from a retracted position to an advanced position within the shell housing 410.

The shell housing 410 includes an outer housing portion 440 and an inner housing portion 442 that are spaced from each other to define an annular cavity 444 (FIG. 35) between the outer and inner housing portions 440 and 442. The staple actuator 412 and the staple pushing member 412a are movable within the annular cavity 444 of the shell housing 410 from a retracted position to an advanced position to eject the staples 420 from the staple cartridge 418.

The annular knife 416 is supported about an outer surface of the knife carrier 414, defines a cylindrical cavity 417, and includes an annular cutting edge 417a. The knife carrier 414 and annular knife 416 are positioned within the through bore 432 of the staple actuator 412 and are movable from retracted positions to advanced positions to cut tissue positioned radially inward of the staple cartridge 418.

The inner housing portion 442 of the shell housing 410 defines a through bore 450 that receives an anvil shaft (not shown) of the anvil assembly 18 (FIG. 1). The through bore 450 has a proximal portion that receives a bushing 452 that defines a through bore 450a that is coaxial with and forms an extension of the through bore 450 of the inner housing portion 442. In embodiments, the bushing 452 is formed of a high strength material, e.g., metal, to provide added strength to the inner housing portion 442 of the shell housing 410 and includes an annular flange 452a. The shell housing 410 includes a proximal portion 458 that supports a coupling mechanism 460 that is operable to releasably couple the reload assembly 400 to the adaptor assembly 14 of the stapling device 10 (FIG. 1). The coupling mechanism 460 allows for removal and replacement of the reload assembly 400 to facilitate reuse of the stapling device 10 (FIG. 1). The coupling mechanism 460 includes a retaining member 462 and a coupling member 464. The coupling member 464 is received about the proximal portion 458 of the shell housing 410 and is configured to engage the distal portion 14a (FIG. 1) of the adaptor assembly 14 to couple the reload assembly 400 to the adaptor assembly 14. It is envisioned that other coupling mechanisms can be used to secure the reload assembly 400 to the adaptor assembly 14. Alternately, the reload assembly 400 can be fixedly secured to the adaptor assembly 14.

The knife carrier 414 includes a plurality of spaced longitudinal body portions 473 that are spaced from each other and together define a central bore 472 (FIG. 35). The central bore 472 of the knife carrier 414 receives the inner housing portion 442 of the shell housing 410 such that the knife carrier 414 is movable about the inner housing portion 442 of the shell housing 410 between a retracted position and an advanced position. The longitudinal body portions 473 of the knife carrier 414 are spaced from each other to define slots 476 that receive guide portions (not shown) of the shell housing 410 to limit the knife carrier 414 to longitudinal movement within the shell housing 410.

The staple actuator 412 includes a body that is also received about the inner housing portion 442 of the shell housing 410 and is movable within the shell housing 410 from a retracted position to an advanced position. The body of the staple actuator 412 defines a plurality of guide slots (not shown) that receive the guide members (not shown) of the shell housing 410 to limit the staple actuator 412 to longitudinal movement within the shell housing 410.

Figure 36:
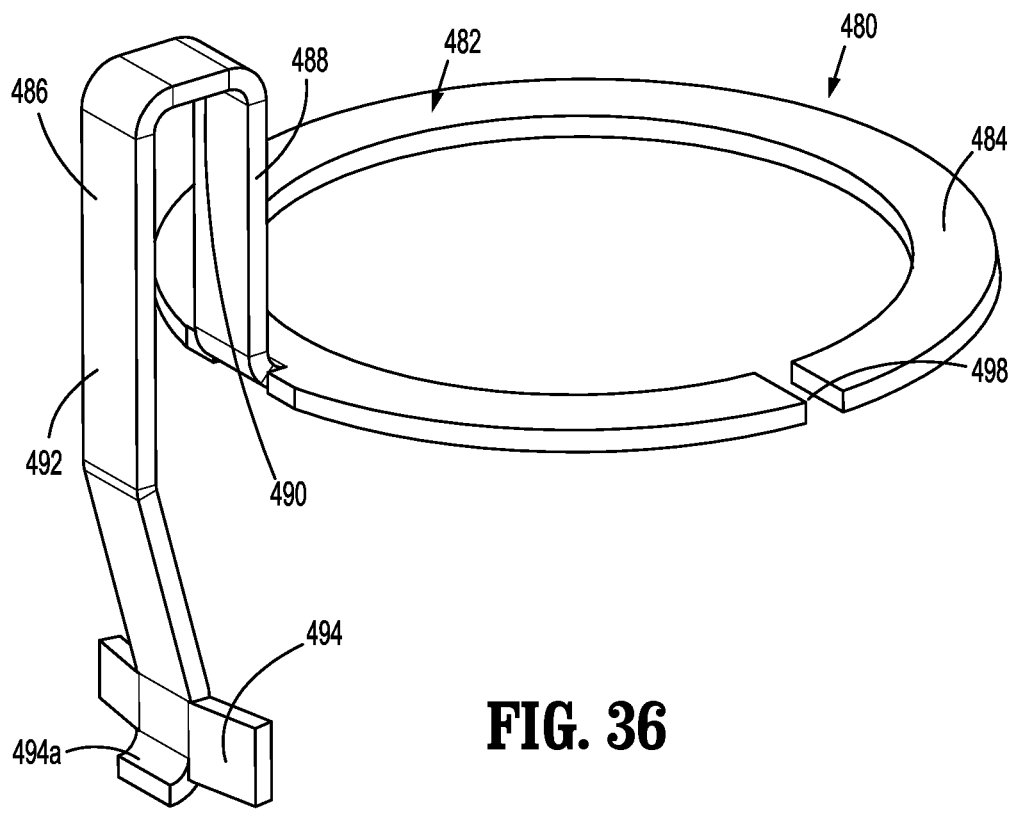
FIG. 36 is a side perspective view of a locking member of the reload assembly shown in FIG. 34.
Figure 37:
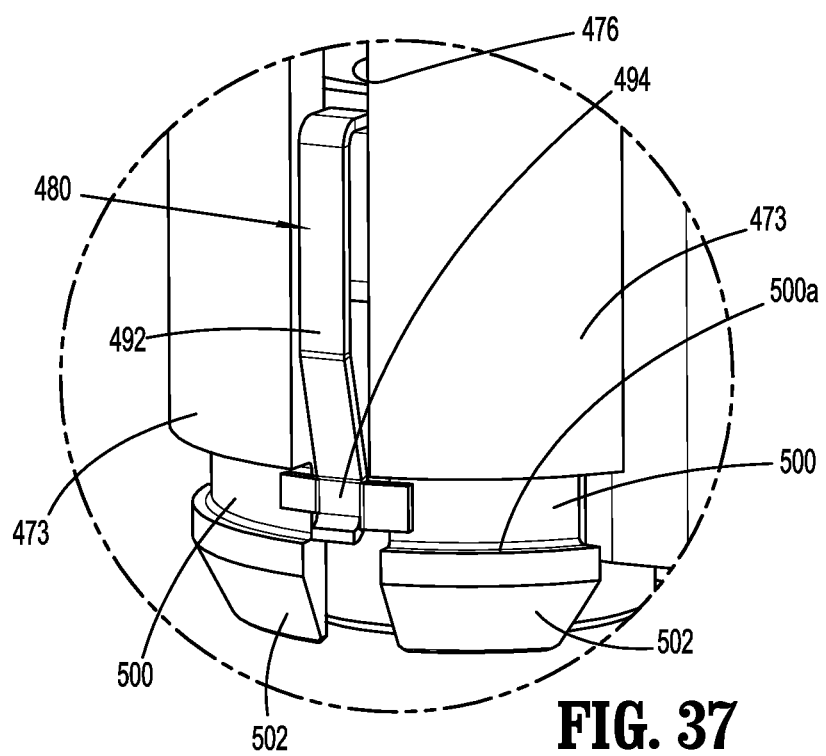
FIG. 37 is an enlarged view of the indicated area of detail shown in FIG. 34.

FIGS. 36 and 37 illustrate a locking member 480 of the reload assembly 400 that includes a body 482 having an annular ring 484 and a lockout latch 486. The annular ring 484 is received about a proximal portion of the bushing 452 (FIG. 35) and is positioned in abutting relation to the flange 452a to secure the locking member 480 to the bushing 452 (FIG. 35). The annular ring 484 of the locking member 480 may include a slot 498 to allow for flexing of the annular ring 480 to facilitate placement of the locking member 480 in a friction fit manner about the bushing 452.

The lockout latch 486 is formed of a resilient material and extends from the annular ring 484. In embodiments, the lockout latch 486 is integrally formed with the annular ring 484 of the locking member 480 and includes a first longitudinal portion 488, a transverse portion 490, and a second longitudinal portion 492. The first longitudinal portion 488 has a first end coupled to the annular ring 484 and extends distally from the annular ring 484. The transverse portion 490 of the lockout latch 486 extends from a second end of the first longitudinal portion 488 radially outward from the bushing 452. The second longitudinal portion 492 extends proximally from the transverse portion 490 and has a proximal end portion that supports a latch member 494. In embodiments, the latch member 494 includes a cam surface 494a that is angled radially outwardly from the second longitudinal portion 492 and defines an axis that is transverse to axes defined by the first and second longitudinal portions 488 and 492 of the locking member 480 and transverse to the transverse portion 490. In embodiments, the locking member 480 can be of integral construction. Alternately, the lockout latch 486 can be pivotably secured to the annular ring 480 using any of a variety of fastening techniques.

In embodiments, the first and second longitudinal portions 488 and 492 are aligned with one of the longitudinal slots 476 defined between the longitudinal body portions 473 of the knife carrier 414 and the transverse portion 490 extends through the respective slot 476. In this configuration, the first longitudinal portion 488 of the locking member 480 is positioned within the knife carrier 414 and the second longitudinal portion 492 is positioned along an outer surface of the knife carrier 414 and supports the latch member 494 in cantilevered fashion.

Figure 38:
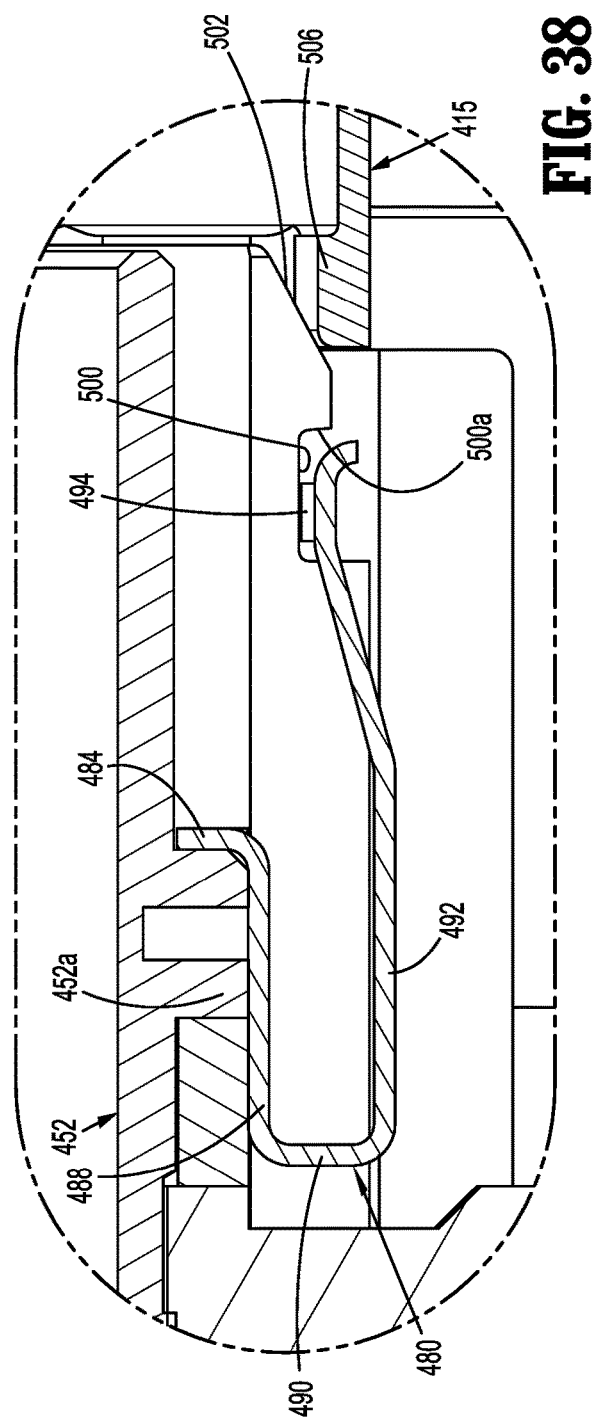
FIG. 38 is an enlarged view of the indicated area of detail shown in FIG. 35 with the knife carrier driver and knife carrier in retracted positions and the locking member in a latched position.

FIGS. 37 and 38 illustrate a proximal portion of the longitudinal body portions 473 of the knife carrier 414. Each of the longitudinal body portions 473 of the knife carrier 414 defines an annular recess 500 and includes a tapered proximal surface 502 that is positioned proximally of the annular recess 500. The annular recess 500 is defined in part by a proximal wall 500a. The knife driver 415 (FIG. 38) of the adaptor assembly 14 (FIG. 1) includes an inner annular rib 506 that is received within the annular recesses 500 of the longitudinal body portions 473 to couple the knife driver 415 to the knife carrier 414 when the stapling device 10 (FIG. 1) is actuated to fire staples (not shown) from the reload assembly 400. The latch member 494 is received within the annular recess 500 (FIG. 37) of the knife carrier 414 when the knife carrier 414 is in a pre-fired retracted position to obstruct distal movement of the knife carrier 414 within the shell housing 410 (FIG. 34). More specifically, the latch member 494 is positioned to engage the proximal wall 500a defining the annular recess 500 in the knife carrier 414 to prevent advancement of the knife carrier 414 within the shell housing 410.

FIGS. 35 and 38 illustrate the reload assembly 400 in the pre-fired state with the knife carrier 414, the knife driver 415, the staple actuator 412, and the staple pushing member 412a in their retracted positions. In the pre-fired state, the distal end of the knife driver 415 is positioned adjacent to a proximal end of the knife carrier 414 and adjacent to the lockout latch 486 of the locking member 480. In this position, the inner annular rib 506 at the distal end portion of the knife driver 415 is spaced proximally of the annular recesses 500 formed in the longitudinal body portions 473 of the knife carrier 414. In addition, the lockout latch 486 is in its undeformed state with the latch member 494 of the lockout latch 486 received within the annular recess 500 of the knife carrier 414. In this position, the latch member 494 is aligned with the proximal wall 500a defining the annular recess 500 to prevent advancement of the knife carrier 414 from its retracted position toward its advanced position. In its retracted position, the annular knife 416 including the cutting edge 417a is shielded within the shell housing 410.

Figure 39:
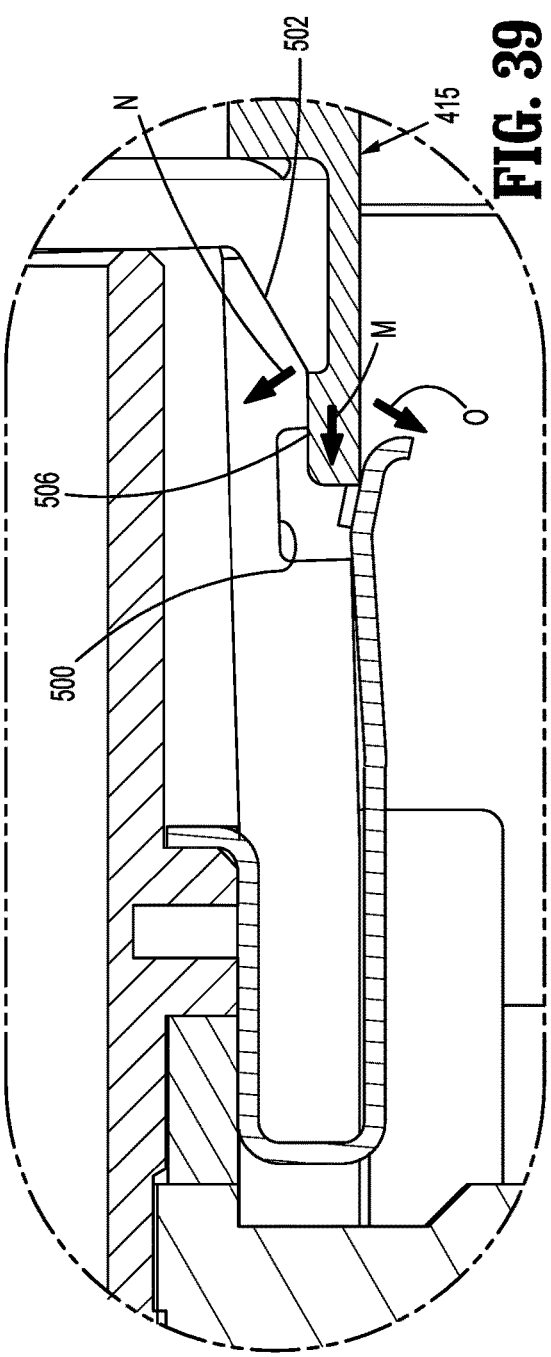
FIG. 39 is an enlarged view of the indicated area of detail shown in FIG. 35 with the knife carrier driver advanced into engagement with the knife carrier and the locking member as the locking member is urged from the latched position.

FIGS. 39-41 illustrate the reload assembly 400 as the knife driver 415 is moved from its retracted position towards its advanced position to move the knife carrier 414 and the annular knife 416 toward their advanced positions. When the knife driver 415 is advanced within the shell housing 410 in the direction indicated by arrow "M" in FIG. 39, the distal end portion of the knife driver 415 engages the tapered surface 502 at the proximal end portion of each of the longitudinal body portions 473 of the knife carrier 414 to urge the longitudinal body portions 473 inwardly in the direction indicated by arrow "N" in FIG. 39. This allows the inner annular rib 506 of the knife driver 515 to pass into the annular recesses 500 of the longitudinal body portions 473 of the knife carrier 414 to couple the distal end portion of the knife driver 415 to the proximal end portion of the knife carrier 414 (FIG. 41).

As the knife driver 415 continues to advance within the shell housing 410 in the direction indicated by arrow "M" in FIGS. 39 and 40, the distal end portion of the knife driver 415 engages the cam surface 494a of the of the latch member 494 to urge the lockout latch 486 outwardly in the direction indicated by arrows "O" towards its deformed state. As the lockout latch 486 moves outwardly away from the bushing 452 to its deformed state, the latch member 494 of the lockout latch 486 is removed from the annular recess 500 formed in the proximal end of the longitudinal body portion 473 of the knife carrier 514 such that the latch member 494 does not obstruct advancement of the knife carrier 414 within the shell housing 410. As such, the knife carrier 414 and the annular knife 416 can be advanced to cut tissue.

FIG. 42 illustrates the reload assembly 400 as the knife carrier 414 and the knife driver 415 are moved from their advanced positions back to their retracted positions in the direction indicated by arrow "P". This movement retracts the annular knife 416 (FIG. 35) into the shell housing 410. When the knife carrier 414 reaches its retracted position and cannot move further proximally through the shell housing 410 (FIG. 35), the longitudinal body portions 473 are forced inwardly by the inner annular rib 506 of the knife driver 415 such that the inner annular rib 506 is removed from the annular recesses 500 of the longitudinal body portions 473 of the knife driver 414 to uncouple the knife driver 415 from the knife carrier 414. In its retracted position, the annular recess 500 of the knife carrier 414 is aligned with the latch member 494 of the lockout latch 486 of the lockout member 480 such that the lockout latch 486 returns to its undeformed state with the latch member 480 received within the annular recess 500 of adjacent longitudinal body portions 473. Once again, the latch member 480 obstructs advancement of the knife carrier 414 to prevent readvancement of the annular knife 216 from within the shell housing 410.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
   an adaptor assembly having a proximal end portion and a distal end portion; and
   a reload assembly supported on the distal end portion of the adaptor assembly, the reload assembly including:
     a shell housing including an outer housing portion and an inner housing portion;
     a staple cartridge supporting staples;
     a staple pusher supported movable from a retracted position to an advanced position to eject the staples from the staple cartridge;
     a staple actuator positioned to engage the staple pusher, the staple actuator having a stop surface and movable from an actuator retracted position to an actuator advanced position to move the staple pusher from a pusher retracted position to a pusher advanced position to eject the staples from the staple cartridge, the staple actuator and the staple pusher defining a through bore;
     a knife carrier supported within the through bore and movable between a carrier retracted position and a carrier advanced position, the knife carrier defining a longitudinal axis and supporting a locking member that is formed from a resilient material, the locking member aligned with the stop surface of the staple actuator when the staple actuator is in the actuator advanced position and the knife carrier is in the carrier retracted position to prevent readvancement of the knife carrier; and
     a knife supported on the knife carrier.

2. The surgical stapling device of claim 1, further including a handle assembly, the proximal end portion of the adaptor assembly supported on the handle assembly.

3. The surgical stapling device of claim 1, wherein the locking member is movable from an undeformed state in which the locking member extends outwardly and distally from the knife carrier to a deformed state in which the locking member is substantially aligned with the longitudinal axis of the knife carrier.

4. The surgical stapling device of claim 3, wherein the locking member is positioned distally of the stop surface of the staple actuator when the staple actuator is in the actuator retracted position and the knife carrier is in the carrier retracted position, the locking member movable from the undeformed state to the deformed state to allow the locking member to move proximally past the stop surface when the staple actuator is in the actuator advanced position and the knife carrier is moved from the carrier advanced position to the carrier retracted position.

5. The surgical stapling device of claim 3, wherein the locking member is supported on the knife carrier in cantilevered fashion.

6. The surgical stapling device of claim 5, wherein the locking member is formed from a flat leaf spring.

7. The surgical stapling device of claim 5, wherein the locking member is formed from wire having a cylindrical cross-section.

8. The surgical stapling device of claim 1, wherein the knife carrier includes a hook member, the hook member aligned with the stop surface of the staple actuator such that movement of the knife carrier from the carrier retracted position to the carrier advanced position moves the staple actuator from the actuator retracted position to the carrier advanced position.

9. The surgical stapling device of claim 1, further including a coupling mechanism, the coupling mechanism coupling the reload assembly to the adaptor assembly to facilitate release of the reload assembly from the adaptor assembly.

10. A reload assembly comprising:
    a shell housing including an outer housing portion and an inner housing portion;
    a staple cartridge supporting staples;
    a staple pusher supported within the shell housing and movable from a retracted position to an advanced position to eject the staples from the staple cartridge;
    a staple actuator supported within the shell housing and positioned to engage the staple pusher, the staple actuator having a stop surface and movable from an actuator retracted position to an actuator advanced position to move the staple pusher from a pusher retracted position to a pusher advanced position to eject the staples from the staple cartridge, the staple actuator and the staple pusher defining a through bore;
    a knife carrier supported within the through bore and movable between a carrier retracted position and a carrier advanced position, the knife carrier defining a longitudinal axis and supporting a locking member formed of a resilient material, the locking member aligned with the stop surface on the staple actuator when the staple actuator is in the actuator advanced position and the knife carrier is in the carrier retracted position to prevent readvancement of the knife carrier; and
    a knife supported on the knife carrier.

11. The reload assembly of claim 10, wherein the shell housing defines a cavity, and the staple pusher, the staple actuator, and the knife carrier are supported within the cavity.

12. The reload assembly of claim 10, wherein the locking member is movable from an undeformed state in which the locking member extends outwardly and distally from the knife carrier to a deformed state in which the locking member is substantially aligned with the longitudinal axis of the knife carrier.

13. The reload assembly of claim 12, wherein the locking member is positioned distally of the stop surface of the staple actuator when the staple actuator is in the actuator retracted position and the knife carrier is in the carrier retracted position, the locking member movable from the undeformed state to the deformed state to allow the locking member to move proximally past the stop surface when the staple actuator is in the actuator advanced position and the knife carrier is moved from the carrier advanced position to the carrier retracted position.

14. The reload assembly of claim 13, wherein the locking member is supported on the knife carrier in cantilevered fashion.

15. The reload assembly of claim 10, wherein the knife carrier includes a hook member, the hook member aligned with the stop surface of the staple actuator such that movement of the knife carrier from the carrier retracted position to the carrier advanced position moves the staple actuator from the actuator retracted position to the carrier advanced position.

16. The reload assembly of claim 15, wherein the locking member is formed from a flat leaf spring.

17. The reload assembly of claim 16, wherein the locking member is formed from wire having a cylindrical cross-section.

18. The reload assembly of claim 10, further including a coupling mechanism, the coupling mechanism adapted to releasably couple the reload assembly to an adaptor assembly of a stapling device to facilitate release of the reload assembly from the stapling device.

19. A reload assembly comprising:
a shell housing;
an annular staple cartridge supporting staples;
a staple actuator supported within the shell housing, the staple actuator having a stop surface and movable from an actuator retracted position to an actuator advanced position to eject the staples from the staple cartridge, the staple actuator defining a through bore;
a knife carrier supported within the through bore and movable between a carrier retracted position and a carrier advanced position, the knife carrier defining a longitudinal axis and supporting a resilient locking member, the resilient locking member aligned with the stop surface on the staple actuator when the staple actuator is in the actuator advanced position and the knife carrier is in the carrier retracted position to prevent readvancement of the knife carrier; and
a knife supported on the knife carrier.

20. The reload assembly of claim 19, wherein the resilient locking member is positioned distally of the stop surface of the staple actuator when the staple actuator is in the actuator retracted position and the knife carrier is in the carrier retracted position, the resilient locking member movable from the undeformed state to the deformed state to allow the resilient locking member to move proximally past the stop surface when the staple actuator is in the actuator advanced position and the knife carrier is moved from the carrier advanced position to the carrier retracted position.

* * * * *